(12) United States Patent
Bilodeau et al.

(10) Patent No.: US 8,067,607 B2
(45) Date of Patent: Nov. 29, 2011

(54) POTASSIUM CHANNEL INHIBITORS

(75) Inventors: Mark T. Bilodeau, Lansdale, PA (US); Jacob M. Hoffman, Lansdale, PA (US); M. Brad Nolt, Blue Bell, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 525 days.

(21) Appl. No.: 12/223,357

(22) PCT Filed: Jan. 29, 2007

(86) PCT No.: PCT/US2007/002458
§ 371 (c)(1),
(2), (4) Date: Jul. 29, 2008

(87) PCT Pub. No.: WO2007/089735
PCT Pub. Date: Aug. 9, 2007

(65) Prior Publication Data
US 2010/0004229 A1     Jan. 7, 2010

Related U.S. Application Data

(60) Provisional application No. 60/764,237, filed on Feb. 1, 2006.

(51) Int. Cl.
*C07D 213/00* (2006.01)
(52) U.S. Cl. ....................................................... 546/264
(58) Field of Classification Search ........................ None
See application file for complete search history.

(56) References Cited

U.S. PATENT DOCUMENTS 4,552,886 A * 11/1985 Krumkalns et al. .......... 514/342
6,303,637 B1 10/2001 Bao et al.

FOREIGN PATENT DOCUMENTS

| WO | 02/24655 A1 | 3/2002 |
|---|---|---|
| WO | 2006/014877 A2 | 2/2006 |
| WO | 2006/015159 A2 | 2/2006 |

OTHER PUBLICATIONS

Han (Advances in Characterization of Pharmaceutical Hydrates. Trends in Bio/Pharmaceutical Industry, pp. 25-29, Mar. 2006).*
Schaefer et al. Failure is not an option: learning from unsuccessful proof-of-concept trials. Drug Discovery Today, 2008, 13 (21/22), 913-916.*
Horig et al. Review: From bench to clinic and back: Perspective on the 1st IQPC Translational Research Conference. Journal of Translational MEdicine, 2004, 2(44).*
J.G. Cannon Chapter Nineteen in Burger's Medicinal Chemistry and Drug Discovery, Fifth Edition, vol. I: Principes and Practice, Wiley-Interscience, 1995, pp. 783-802.*
Bilodeau, Mark T., Potent N-(1,3-Thiazol-2-yl)pyridine-2-amine Vascular Endothelial Growth Factor Receptor Tyrosine Kinase Inhibitors with Excellent Pharmacokinetics and Low Affinity for the hERG Ion Channel, J. Med. Chem., 2004, vol. 47, pp. 6363-6372.
Decher, Niels et al., Molecular Basis for Kv1.5 Channel Block, The Journal of Biological Chemistry, 2004, vol. 279, No. 1, pp. 394-400.
Peukert, Stefan et al., Identification, Synthesis, and Activity of Novel Blockers of the Voltage-Gated Potassium Channel Kv1.5, J. Med. Chem., 2003, vol. 46, pp. 486-498.
Knobloch, Karsten et al., Electrophysiological and antiarrhythmic effects of the novel IKur channel blockers, S9947 and 520951, on left vs. right pig atrium in vivo in comparison with the IKr blockers dofetilide, azimilide, d,I-sotalol and ibutilide, Naunyn-Schmiedeberg's Arch Pharmacol., 2002, vol. 366, pp. 482-487.

* cited by examiner

*Primary Examiner* — Brandon Fetterolf
*Assistant Examiner* — Anna Pagonakis
(74) *Attorney, Agent, or Firm* — Heidi M. Struse; Richard S. Parr; Mark R. Daniel

(57) ABSTRACT

The present invention relates to pyridin-3-yl pyridin-3-amine compounds and derivatives thereof having the structure formula (I) useful as potassium channel inhibitors to treat cardiac arrhythmias, and the like.

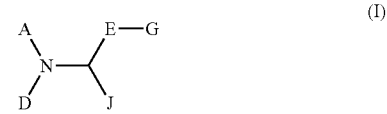

5 Claims, No Drawings

US 8,067,607 B2

POTASSIUM CHANNEL INHIBITORS

PRIORITY CLAIM

This application is a §371 National Stage Application of PCT/US2007/002458, filed on Jan. 29, 2007, which claims priority from U.S. Provisional Application Ser. No. 60/764,237, filed on Feb. 1, 2006.

BACKGROUND OF THE INVENTION

The present invention relates broadly to compounds that are useful as potassium channel inhibitors. Compounds in this class may be useful as Kv1.5 antagonists for treating and preventing cardiac arrhythmias, and the like.

Atrial fibrillation (AF) is the most common sustained cardiac arrhythmia in clinical practice and is likely to increase in prevalence with the aging of the population. While AF is rarely fatal, it can impair cardiac function and lead to complications such as the development of congestive heart failure, thromboembolism, or ventricular fibrillation.

Currently available antiarrhythmic agents have been developed for the treatment of ventricular and atrial/supraventricular arrhythmias. Malignant ventricular arrhythmias are immediately life-threatening and require emergency care. Drug therapy for ventricular arrhythmia includes Class Ia (eg. procainamide, quinidine), Class Ic (eg. flecainide, propafenone), and Class III (amiodarone) agents, which pose significant risks of proarrhythmia. These Class I and III drugs have been shown to convert AF to sinus rhythm and to prevent recurrence of AF (Mounsey, J P, DiMarco, J P, *Circulation*, 102:2665-2670), but pose an unacceptable risk of potentially lethal ventricular proarrhythmia and thus may increase mortality (Pratt, C M, Moye, L A, *Am J. Cardiol.*, 65:20B-29B, 1990; Waldo et al, *Lancet*, 348:7-12, 1996; Torp-Pedersen et al, *Expert Opin. Invest. Drugs*, 9:2695-2704, 2000). These observations demonstrate a clear unmet medical need to develop safer and more efficacious drugs for the treatment of atrial arrhythmias. Class m antiarrhythmic agents cause a selective prolongation of the APD without significant depression of cardiac conduction or contractile function. The only selective Class III drug approved for clinical use in atrial fibrillation is dofetilide, which mediates its anti-arrhythmic effects by blocking $I_{Kr}$, the rapidly activating component of $I_K$ found in both atrium and ventricle in humans (Mounsey, J P, DiMarco, J P, *Circulation*, 102:2665-2670). Since $I_{Kr}$ blockers increase APD and refractoriness both in atria and ventricle without affecting conduction per se, theoretically they represent potentially useful agents for the treatment of arrhythmias like AF (Torp-Pedersen, et al, *Expert Opin. Invest. Drugs*, 9:2695-2704, 2000). However, these agents have the major liability of an enhanced risk of proarrhythmia at slow heart rates.

The ultrarapid delayed rectifier K⁺ current, $I_{Kur}$, has been observed specifically in human atrium and not in ventricle. The molecular correlate of $I_{Kur}$ in the human atrium is the potassium channel designated Kv1.5. $I_{Kur}$ is believed to contribute significantly to repolarization in human atrium. Consequently, a specific blocker of $I_{Kur}$, that is a compound which blocks Kv1.5, would overcome the shortcoming of other compounds by prolonging refractoriness through retardation of the repolarization in the human atrium without causing the delays in ventricular repolarization that underlie arrhythmogenic after depolarizations and acquired long QT syndrome observed during treatment with current Class III drugs. Kv1.5 blockers exhibiting these properties have been described (Peukert et al, *J. Med. Chem.*, 46:486-498, 2003; Knobloch et al, *Naunyn-Schmedieberg's Arch. Pharmacol.* 366:482-287, 2002; Merck & Co., Inc. WO0224655, 2002).

The compounds described in this invention are Kv1.5 antagonists.

SUMMARY OF THE INVENTION

The invention concerns compounds of Formula I which antagonize the Kv1.5 potassium channel:

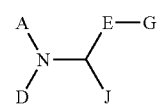

The compounds of this invention are useful in the treatment and prevention of cardiac arrhythmias, and the like. Also within the scope of this invention are pharmaceutical formulations comprising a compound of Formula I and a pharmaceutical carrier.

DETAILED DESCRIPTION OF THE DISCLOSURE

The invention includes compounds of Formula 1:

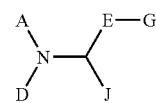

or a pharmaceutically acceptable salt, wherein:
A and L are independently selected from the group consisting of
1) an aryl ring,
2) a heteroaryl ring, wherein the point of attachment to the heteroaryl ring is a carbon atom, and the heteroaryl ring is selected from the group consisting of:
   a) a 5-membered unsaturated monocyclic ring with 1, 2, 3, or 4 heteroatom ring atoms selected from the group consisting of N, O or S,
   b) a 6-membered unsaturated monocyclic ring with 1, 2, 3, or 4 heteroatom ring atoms selected from the group consisting of N, O or S, and
   c) an 8-, 9- or 10-membered saturated or unsaturated bicyclic ring with 1, 2, 3, or 4 heteroatom ring atoms selected from the group consisting of N, O or S;
3) $C_1$-$C_2$ alkyl, wherein any stable atom is independently unsubstituted or substituted with a group selected from $R^4$,
4) a $C_3$-$C_{10}$ cycloalkyl ring, wherein any stable ring atom is independently unsubstituted or substituted with a group selected from $R^4$, and
5) a 4-6 membered saturated heterocyclic ring with 1, 2 or 3 heteroatom ring atoms selected from the group consisting of N, O and S,
said aryl, heteroaryl, cycloalkyl, and saturated heterocyclic ring is unsubstituted, mono-substituted with $R^4$, disubstituted with groups independently selected from $R^4$, trisubstituted with groups independently selected from $R^4$, or tetrasubstituted with groups independently selected from $R^4$, and wherein any stable S or N heteroaryl or heterocyclic ring atom is unsubstituted or substituted with oxo;

D is
- 1) an aryl ring, or
- 2) a heteroaryl ring, wherein the point of attachment to the heteroaryl ring is a carbon atom or a nitrogen atom, and wherein the heteroaryl ring is selected from the group consisting of
  - a) a 5-membered unsaturated monocyclic ring with 1, 2, 3, or 4 heteroatom ring atoms selected from the group consisting of N, O or S,
  - b) a 6-membered unsaturated monocyclic ring with 1, 2, 3, or 4 heteroatom ring atoms selected from the group consisting of N, O or S, and
  - c) an 8-, 9- or 10-membered unsaturated bicyclic ring with 1, 2, 3, or 4 heteroatom ring atoms selected from the group consisting of N, O or S, said aryl or heteroaryl ring is unsubstituted, mono-substituted with $R^4$, disubstituted with groups independently selected from $R^4$, trisubstituted with groups independently selected from $R^4$, or tetrasubstituted with groups independently selected from $R^4$, and wherein any stable S or N heteroaryl ring atom is unsubstituted or substituted with oxo;

E is selected from the group consisting of
- 1) an aryl ring, wherein any stable aryl ring atom is independently unsubstituted or substituted with a group selected from $R^4$,
- 2) a heteroaryl ring, wherein the point of attachment to the heteroaryl ring is a carbon atom or a nitrogen atom, and the heteroaryl ring is selected from the group consisting of:
  - a) a 5-membered unsaturated monocyclic ring with 1,2, 3,or 4 heteroatom ring atoms selected from the group consisting of N, O or S,
  - b) a 6-membered unsaturated monocyclic ring with 1,2, 3,or 4 heteroatom ring atoms selected from the group consisting of N, O or S, and
  - c) an 8-, 9- or 10-membered unsaturated bicyclic ring with 1,2,3,or 4 heteroatom ring atoms selected from the group consisting of N, O or S;
- 3) a $C_3$-$C_{10}$ cycloalkyl ring, wherein any stable ring atom is independently unsubstituted or substituted with a group selected from $R^4$, and
- 4) a 4-6 membered saturated heterocyclic ring with 1, 2 or 3 heteroatom ring atoms selected from the group consisting of N, O and S, wherein any stable ring atom is independently unsubstituted or substituted with a group selected from $R^4$, said aryl, heteroaryl, cycloalkyl, and saturated heterocyclic ring is unsubstituted, mono-substituted with $R^4$, disubstituted with groups independently selected from $R^4$, trisubstituted with groups independently selected from $R^4$, or tetrasubstituted with groups independently selected from $R^4$, and wherein any stable S or N heteroaryl or heterocyclic ring atom is unsubstituted or substituted with oxo;

G, attached to a carbon or nitrogen ring atom of ring E, is selected from the group consisting of halogen,
—NH-L,
—N($SO_2C_{1-6}$alkyl)-L,
—N($C_{1-6}$alkyl)-L,
—NHC(O)NH-L,
—NH(C(O)$C_{1-6}$alkyl)-L,
—O-L,
—S-L,
—$SO_2$-L,
—C(O)NH-L,
—$C_{1-6}$alkylene-L, and
-L
wherein $C_{1-6}$alkyl and $C_{1-6}$alkylene are unsubstituted or substituted with halogen;

J is selected from the group consisting of H, F, $C_{1-6}$ alkyl, CN, and CF3;

Ra, in each instance in which it appears, is independently selected from the group consisting of
1) hydrogen,
2) $C_1$-$C_6$ alkyl,
3) halogen,
4) aryl,
5) heterocycle,
6) $C_3$-$C_{10}$ cycloalkyl,
7) $OR^5$, and
8) $CH_2OR^5$,
said alkyl, aryl, heterocycle and cycloalkyl is unsubstituted or substituted with at least one substituent selected from $R^6$;

$R^4$, in each instance in which it appears, is independently selected from the group consisting of
1) hydrogen,
2) halogen,
3) $NO_2$,
4) CN,
5) $CR^4$=$C(R^5)_2$,
6) C≡$CR^5$,
7) $(CR^a{}_2)_n OR^5$,
8) $(CR^a{}_2)_n N(R^5)_2$,
9) $(CR^a{}_2)_n C(O)R^5$,
10) $(CR^a{}_2)_n C(O)OR^5$,
11) $(CR^a{}_2)_n R^5$,
12) $(CR^a{}_2)_n S(O)_m R^5$,
13) $(CR^a{}_2)_n S(O)_m N(R^5)_2$,
14) $OS(O)_m R^5$,
15) $N(R^5)C(O)R^5$,
16) $N(R^5)S(O)_m R^5$,
17) $(CR^a{}_2)_n N(R^6)R^5$,
18) $(CR^a{}_2)_n N(R^5)(CR^a{}_2)_n C(O)N(R^5)_2$,
19) $(CR^a{}_2)_n N(R^5)(CR^a{}_2)_n C(O)OR^5$,
20) $N(R^5)(CR^a{}_2)_n R^5$,
21) $N(R^5)(CR^a{}_2)_n N(R^5)_2$,
22) $(CR^a{}_2)_n C(O)N(R^5)_2$,
23) $(CR^a{}_2)_n C(O)NH(CR^a{}_2)_n R^5$,
24) $(CR^a{}_2)_n C(O)NHC(R^5)_2(CR^a{}_2)_n N(R^5)_2$ and
25) $C(O)NH(CR^a{}_2)(CR^a{}_3)$;

$R^5$, in each instance in which it appears, is independently selected from the group consisting of
1) hydrogen,
2) unsubstituted or substituted $C_1$-$C_6$ alkyl,
3) unsubstituted or substituted $C_3$-$C_{10}$ cycloalkyl,
4) unsubstituted or substituted aryl,
5) unsubstituted or substituted heterocycle,
6) $CF_3$,
7) unsubstituted or substituted $C_2$-$C_6$ alkenyl, and
8) unsubstituted or substituted $C_2$-$C_6$ alkynyl,
or in the case where $R^5$ is attached to a nitrogen atom that is disubstituted with $R^5$, each $R^5$ is independently selected from $C_1$-$C_6$ alkyl, and the nitrogen atom together with each $R^5$ form a ring;

$R^6$, in each instance in which it appears, is independently selected from the group consisting of
1) hydrogen,
2) unsubstituted or substituted $C_1$-$C_6$ alkyl,
3) halogen,
4) oxo,
5) $OR^5$, 6) CF$_3$,
7) unsubstituted or substituted aryl,
8) unsubstituted or substituted C$_3$-C$_{10}$ cycloalkyl,
9) unsubstituted or substituted heterocycle,
10) S(O)$_m$N(R$^5$)$_2$,
11) C(O)OR$^5$,
12) C(O)R$^5$,
13) CN,
14) C(O)N(R$^5$)$_2$,
15) N(R$^5$)C(O)R$^5$,
16) N(R$^5$)C(O)OR$^5$,
17) N(R$^5$)C(O)N(R$^5$)$_2$,
18) OC(O)N(R$^5$)$_2$,
19) S(O)$_m$R$^5$,
20) OS(O)$_m$R$^5$,
21) NO$_2$,
22) N(R$^5$)$_2$;
23) SC(O)R$^5$,
24) N(R$^5$)S(O)$_m$R$^5$, m is independently 0, 1 or 2; and n, in each instance in which it occurs, is independently selected from 0, 1, 2, 3, 4, 5 or 6.

In another embodiment of the compounds of Formula 1, or a pharmaceutically acceptable salt thereof, A is selected from the group consisting of 1) an aryl ring, and
2) a heteroaryl ring, wherein the point of attachment to the heteroaryl ring is a carbon atom, and the heteroaryl ring is a 6-membered unsaturated monocyclic ring with 1, 2, 3, or 4 heteroatom ring atoms selected from the group consisting of N, O or S, wherein said aryl or unsaturated heteroaryl ring is unsubstituted, mono-substituted with R$^4$, disubstituted with groups independently selected from R$^4$, trisubstituted with groups independently selected from R$^4$, or tetrasubstituted with groups independently selected from R$^4$, and wherein any stable S or N heteroaryl or heterocyclic ring atom is unsubstituted or substituted with oxo.

In a preferred group of this embodiment A is selected from the group consisting of 1) an aryl ring,
2) a heteroaryl ring, wherein the point of attachment to the heteroaryl ring is a carbon atom, and the heteroaryl ring is a 6-membered unsaturated monocyclic ring with 1, 2, 3, or 4 heteroatom ring atoms selected from the group consisting of N, O or S, and said aryl or unsaturated heteroaryl ring is unsubstituted or mono-substituted with R$^4$.

In a more preferred group of this embodiment A is selected from the group consisting of 1) an aryl ring,
2) a heteroaryl ring, wherein the point of attachment to the heteroaryl ring is a carbon atom, and the heteroaryl ring is a 6-membered unsaturated monocyclic ring with 1, 2, 3, or 4 heteroatom ring atoms selected from the group consisting of N, O or S, and said aryl or unsaturated heteroaryl ring is unsubstituted or mono-substituted with —(CR$^a$$_2$)$_n$S(O)$_m$R$^5$.

In a more preferred group of this embodiment A is selected from the group consisting of

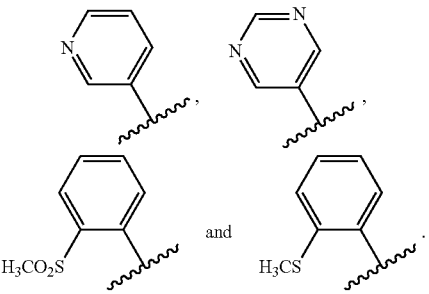

Within these subsets of A, all other variables are as originally defined.

In another embodiment of the compounds of Formula I, or a pharmaceutically acceptable salt thereof, D is selected from the group consisting of 1) an aryl ring, and
2) a heteroaryl ring, wherein the point of attachment to the heteroaryl ring is a carbon atom or a nitrogen atom, and wherein the heteroaryl ring is selected from the group consisting of a 6-membered unsaturated monocyclic ring with 1, 2, 3, or 4 heteroatom ring atoms selected from the group consisting of N, O or S, wherein said aryl or heteroaryl ring is unsubstituted, mono-substituted with R$^4$, disubstituted with groups independently selected from R$^4$, trisubstituted with groups independently selected from R$^4$, or tetrasubstituted with groups independently selected from R$^4$, and wherein any stable S or N heteroaryl ring atom is unsubstituted or substituted with oxo.

In a preferred group of this embodiment D is selected from the group consisting of 1) an aryl ring, and
2) a heteroaryl ring, wherein the point of attachment to the heteroaryl ring is a carbon atom or a nitrogen atom, and wherein the heteroaryl ring is selected from the group consisting of a 6-membered unsaturated monocyclic ring with 1, 2, 3, or 4 heteroatom ring atoms selected from the group consisting of N, O or S, wherein said aryl or heteroaryl ring is unsubstituted or mono-substituted with R$^4$, and wherein any stable N heteroaryl ring atom is unsubstituted or substituted with oxo.

In a more preferred group of this embodiment D is selected from the group consisting of 1) an aryl ring, and
2) a heteroaryl ring, wherein the point of attachment to the heteroaryl ring is a carbon atom or a nitrogen atom, and wherein the heteroaryl ring is selected from the group consisting of a 6-membered unsaturated monocyclic ring with 1, 2, 3, or 4 heteroatom ring atoms selected from the group consisting of N, O or S, wherein said aryl or heteroaryl ring is unsubstituted or mono-substituted with CN, —(CR$^a$$_2$)$_n$OR$^5$, —(CR$^a$$_2$)$_n$S(O)$_m$R$^5$, and wherein any stable N heteroaryl ring atom is unsubstituted or substituted with oxo.

In a more preferred group of this embodiment D is selected from the group consisting of

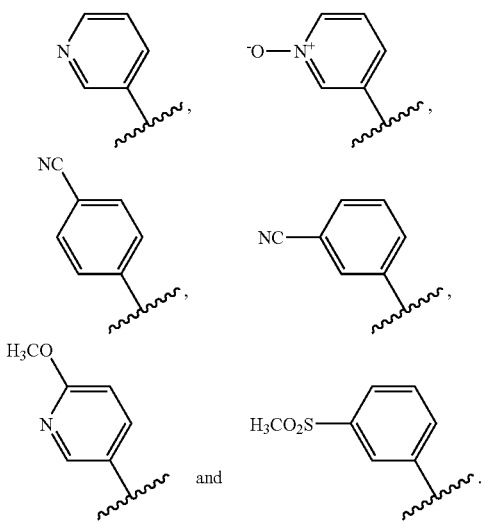

and

Within these subsets of D, all other variables are as originally defined.

In another embodiment of the compounds of Formula I, or a pharmaceutically acceptable salt thereof, E is selected from the group consisting of
1) an aryl ring, and
2) a heteroaryl ring, wherein the point of attachment to the heteroaryl ring is a carbon atom or a nitrogen atom, and the heteroaryl ring is selected from the group consisting of a 6-membered unsaturated monocyclic ring with 1,2, 3,or 4 heteroatom ring atoms selected from the group consisting of N, O or S, and wherein said aryl or heteroaryl ring is unsubstituted, monosubstituted with $R^4$, disubstituted with groups independently selected from $R^4$, trisubstituted with groups independently selected from $R^4$, or tetrasubstituted with groups independently selected from $R^4$, and wherein variable G is attached to a ring carbon atom, and wherein any stable S or N heteroaryl or heterocyclic ring atom is unsubstituted or substituted with oxo.

In a preferred group of this embodiment E is selected from the group consisting of
1) an aryl ring, and
2) a heteroaryl ring, wherein the point of attachment to the heteroaryl ring is a carbon atom or a nitrogen atom, and the heteroaryl ring is selected from the group consisting of a 6-membered unsaturated monocyclic ring with 1,2, 3,or 4 heteroatom ring atoms selected from the group consisting of N, O or S, and wherein said aryl or heteroaryl ring is unsubstituted, and wherein variable G is attached to a ring carbon atom.

In a more preferred group of this embodiment E-G is selected from the group consisting of

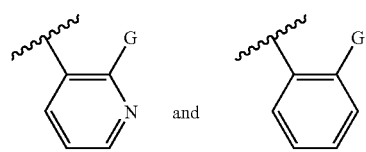

and

Within these subsets of E and E-G, all other variables are as originally defined.

In another embodiment of the compounds of Formula I, or a pharmaceutically acceptable salt thereof, G is selected from the group consisting of
halogen,
—NH-L,
—N(CH$_3$)-L, and
-L.

In a preferred group of this embodiment G is selected from the group consisting of

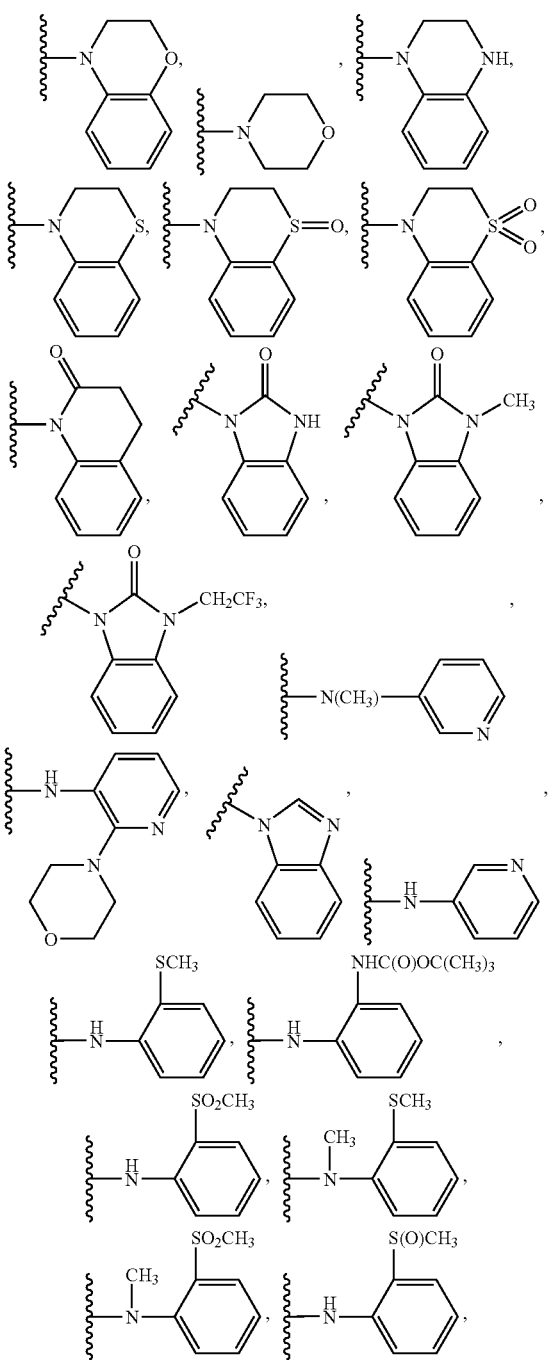

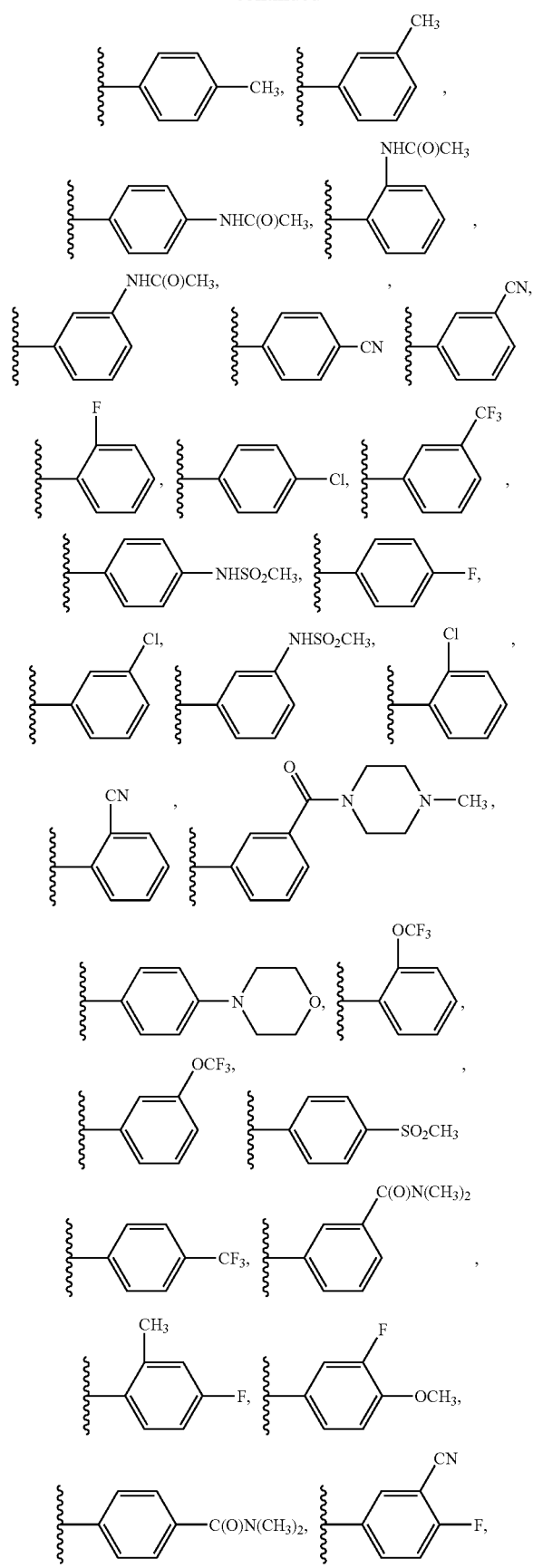

-continued

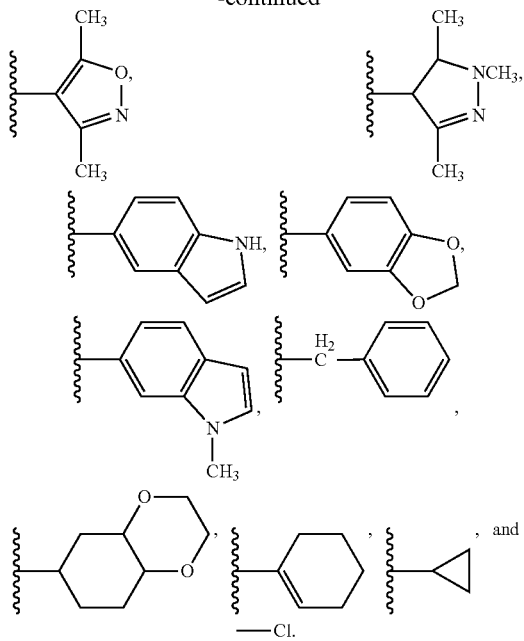

Within these subsets of G, all other variables are as originally defined.

In another embodiment of the compounds of Formula I, or a pharmaceutically acceptable salt thereof, L is selected from the group consisting of -continued

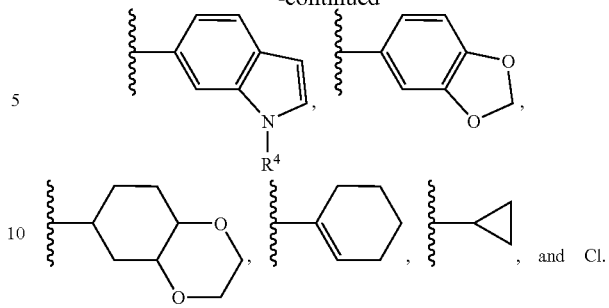

Within this subset of L, all other variables are as originally defined.

In another embodiment of the compounds of Formula I, or a pharmaceutically acceptable salt thereof, J is selected from the group consisting of hydrogen and $C_{1-6}$ alkyl In a preferred group of this embodiment J is selected from the group consisting of hydrogen and —$CH_3$.

Within these subsets of J, all other variables are as originally defined.

Another embodiment of the invention includes a compound selected from the group consisting of:

1. N-{[2-(2,3-dihydro-4H-1,4-benzoxazin-4-yl)pyridin-3-yl]methyl}-N-pyridin-3-ylpyridin-3-amine
2. 3-[(dipyridin-3-ylamino)methyl]-N-methyl-N-pyridin-3-ylpyridin-2-amine
3. 3-[(dipyridin-3-ylamino)methyl]-N-(2-morpholin-4-ylpyridin-3-yl)pyridin-2-amine
4. N-[(2-morpholin-4-ylpyridin-3-yl)methyl]-N-pyridin-3-ylpyridin-3-amine
5. N-{[2-(3,4-dihydroquinoxalin-1(2H)-yl)pyridin-3-yl]methyl}-N-pyridin-3-ylpyridin-3-amine
6. N-{[2-(1H-benzimnidazol-1-yl)pyridin-3-yl]methyl}-N-pyridin-3-ylpyridin-3-amine
7. 3-[(dipyridin-3-ylamino)methyl]-N-pyridin-3-ylpyridin-2-amine
8. N-{[2-(2,3-dihydro-4H-1,4-benzothiazin-4-yl)pyridin-3-yl]methyl}-N-pyridin-3-ylpyridin-3-amine
9. N-{[2-(1-oxido-2,3-dihydro-4H-1,4-benzothiazin-4-yl)pyridin-3-yl]methyl}-N-pyridin-3-ylpyridin-3-amino
10. N-{[2-(1,1-dioxido-2,3-dihydro-4H-1,4-benzothiazin-4-yl)pyridin-3-yl]methyl}-N-pyridin-3-ylpyridin-3-amine 1-oxide
11. N-{[2-(1,1-dioxido-2,3-dihydro-4H-1,4-benzothiazin-4-yl)pyridin-3-yl]methyl}-N-pyridin-3-ylpyridin-3-amine
12. N-{2-[(dipyridin-3-ylamino)methyl]phenyl}-N-methylpyridin-3-amine
13. 4-[{[2-(2,3-dihydro-4H-1,4-benzothiazin-4-yl)pyridin-3-yl]methyl}(pyridin-3-yl)amino]benzonitrile
14. 4-[{[2-(1H-benzimidazol-1-yl)pyridin-3-yl]methyl}(pyridin-3-yl)amino]benzonitrile
15. N-{[2-(1H-benzimidazol-1-yl)pyridin-3-yl]methyl}-N-pyridin-3-ylpyrimidin-5-amine
16. 4-[{[2-(1,1-dioxido-2,3-dihydro4H-1,4-benzothiazin-4-yl)pyridin-3-yl]methyl}(pyridin-3-yl)amino]benzonitrile
17. N-[2-(2,3-dihydro-4H-1,4-benzothiazin4-yl)benzyl]-N-pyridin-3-ylpyridin-3-amine
18. N-[2-(1,1-dioxido-2,3-dihydro-4H-1,4-benzothiazin-4-yl)benzyl]-N-pyridin-3-ylpyridin-3-amine
19. 3-[{[2-(2,3-dihydro-4H-1,4-benzothiazin-4-yl)pyridin-3-yl]methyl}(pyridin-3-yl)amino]benzonitrile
20. N-{[2-(1H-benzimidazol-1-yl)pyridin-3-yl]methyl}-6-methoxy-N-pyridin-3-ylpyridin-3-amine 21. N-{[2-(2,3-dihydro-4-1,4-benzothiazin-4-yl)pyridin-3-yl]methyl}-N-pyridin-3-ylpyrimidin-5-amine
22. 3-[{[2-(1,1-dioxido-2,3-dihydro-4H-1,4-benzothiazin-4-yl)pyridin-3-yl]methyl}(pyridin-3-yl)amino]benzonitrile
23. 3-[(dipyridin-3-ylamino)methyl]-N-[2-(methylthio)phenyl]pyridin-2-amine
24. tert-butyl[2-({3-[(dipyridin-3-ylamino)methyl]pyridin-2-yl}amino)phenyl]carbamate
25. 1-{3-[(dipyridin-3-ylamino)methyl]pyridin-2-yl}-1,3-dihydro-2H-benzimidazol-2-one
26. 3-[(dipyridin-3-ylamino)methyl]-N-[2-(methylsulfonyl)phenyl]pyridin-2-amine
27. N-{[2-(1,1-dioxido-2,3-dihydro-4H-1,4-benzothiazin-4-yl)pyridin-3-yl]methyl}-N-pyridin-3-ylpyrimidin-5-amine
28. N-{[2-(1-oxido-2,3-dihydro-4H-1,4-benzothiazin-4-yl)pyridin-3-yl]methyl}-N-pyridin-3-ylpyrimidin-5-amine
29. 3-[(dipyridin-3-ylamino)methyl]-N-methyl-N-[2-(methylthio)phenyl]pyridin-2-amine
30. 3-[(dipyridin-3-ylamino)methyl]-N-methyl-N-[2-(methylsulfonyl)phenyl]pyridin-2-amine
31. 3-[{[2-(1H-benzimidazol-1-yl)pyridin-3-yl]methyl}(pyridin-3-yl)amino]benzonitrile
32. 3-[[(2-{[2-(methylsulfonyl)phenyl]amino} pyridin-3-yl)methyl](pyridin-3-yl)arnino]benzonitrile
33. 3-[[(2-{[2-(methylthio)phenyl]amino}pyridin-3-yl)methyl](pyridin-3-yl)amino]benzonitrile
34. 1-{3-[(dipyridin-3-ylamino)methyl]pyridin-2-yl}-3-methyl-1,3-dihydro-2H-benzimidazol-2-one
35. N-{[2-(2,3-dihydro-4H-1,4-benzothiazin-4-yl)pyridin-3-yl]methyl}-N-[3-(methylsulfonyl)phenyl]pyridin-3-amine
36. 3-{[[3-(methylsulfonyl)phenyl](pyridin-3-yl)amino]methyl}-N-[2-(methylthio)phenyl]pyridin-2-amine
37. N-{[2-(1,1-dioxido-2,3-dihydro-4H-1,4-benzothiazin-4-yl)pyridin-3-yl]methyl}-N-[3-(methylsulfonyl)phenyl]pyridin-3-amine
38. N-[2-(methylsulfonyl)phenyl]-3-{[[3-(methylsulfonyl)phenyl](pyridin-3-yl)amino]methyl}pyridin-2-amine
39. N-(2-{[2-(methylsulfonyl)phenyl]amino}benzyl)-N-pyridin-3-ylpyridin-3-amine
40. 3-{[(6-methoxypyridin-3-yl)(pyridin-3-yl)amino]methyl}-N-[2-(methylthio)phenyl]pyridin-2-amine
41. N-{[2-(2,3-dihydro4H-1,4-benzothiazin4-yl)pyridin-3-yl]methyl}-6-methoxy-N-pyridin-3-ylpyridin-3-amine
42. 3-{[(6-methoxypyridin-3-yl)(pyridin-3-yl)amino]methyl}-N-[2-(methylsulfinyl)phenyl]pyridin-2-amine
43. 3-{[(6-methoxypyridin-3-yl)(pyridin-3-yl)amino]methyl}-N-[2-(methylsulfonyl)phenyl]pyridin-2-amine
44. 6-methoxy-N-{[2-(1-oxido-2,3-dihydro-4H-1,4-benzothiazin4-yl)pyridin-3-yl]methyl}-N-pyridin-3-ylpyridin-3-amine
45. N-{[2-(1,1-dioxido-2,3-dihydro-4H-1,4-benzothiazin-4-yl)pyridin-3-yl]methyl}-6-methoxy-N-pyridin-3-ylpyridin-3-amine
46. 3-[{[2-(2,3-dihydro-4H-1,4-benzothiazin-4-yl)pyridin-3-yl]methyl}(pyrimidin-5-yl)amino]benzonitrile
47. 1-{3-[(dipyridin-3-ylamino)methyl]pyridin-2-yl}-3,4-dihydroquinolin-2(1H)-one
48. N-[2-(1,1-dioxido-2,3-dihydro-4H-1,4-benzothiazin-4-yl)benzyl]-N-[3-(methylsulfonyl)phenyl]pyridin-3-amine
49. 3-[{[2-(3-methyl-2-oxo-2,3-dihydro-1H-benzimidazol-1-yl)pyridin-3-yl]methyl}(pyrimidin-5-yl)amino]benzonitrile
50. 3-[{[2-(3-methyl-2-oxo-2,3-dihydro-1H-benzimidazol-1-yl)pyridin-3-yl]methyl}(pyridin-3-yl)amino]benzonitrile
51. N-{[2-(2,3-dihydro-4H-1,4-benzothiazin-4-yl)pyridin-3-yl]methyl}-3-(methylsulfonyl)-N-[3-(methylsulfonyl)phenyl]aniline
52. 1-{3-[(dipyridin-3-ylamino)methyl]pyridin-2-yl}-3-(2,2,2-trifluoroethyl)-1,3-dihydro-2H-benzimidazol-2-one
53. N-[1-(4-methylbiphenyl-2-yl)ethyl]-N-pyridin-3-ylpyridin-3-amine
54. N-[1-(3-methylbiphenyl-2-yl)ethyl]-N-pyridin-3-ylpyridin-3-amine
55. N-{2-[1-(dipyridin-3-ylamino)ethyl]biphenyl-4-yl}acetamide
56. N-{1-[2-(1H-indol-5-yl)phenyl]ethyl}-N-pyridin-3-ylpyridin-3-amine
57. N-{2-[1-(dipyridin-3-ylamino)ethyl]biphenyl-2-yl}acetamide
58. N-pyridin-3-yl-N-[1-(2-pyridin-3-ylphenyl)ethyl]pyridin-3-amine
59. N-{1-[2-(1-methyl-1H-pyrazol-4-yl)phenyl]ethyl}-N-pyridin-3-ylpyridin-3-amine
60. N-{2-[1-(dipyridin-3-ylamino)ethyl]biphenyl-3-yl}acetamide
61. N-{-[2-(1-benzyl-1H-pyrazol-4-yl)phenyl]ethyl}-N-pyridin-3-ylpyridin-3-amine
62. N-pyridin-3-yl-N-[1-(2-pyridin-4-ylphenyl)ethyl]pyridin-3-amine
63. 2-[1-(dipyridin-3-ylamino)ethyl]biphenyl-4-carbonitrile
64. 2-[1-(dipyridin-3-ylamino)ethyl]biphenyl-3-carbonitrile
65. N-[1-(2-fluorobiphenyl-2-yl)ethyl]-N-pyridin-3-ylpyridin-3-amine
66. N-[1-(4-chlorobiphenyl-2-yl)ethyl]-N-pyridin-3-ylpyridin-3-amine
67. N-[1-(2-benzylphenyl)ethyl]-N-pyridin-3-ylpyridin-3-amine
68. N-{1-[2-(6-methoxypyridin-3-yl)phenyl]ethyl}-N-pyridin-3-ylpyridin-3-amine
69. N-pyridin-3-yl-N-{1-[3-(trifluoromethyl)biphenyl-2-yl]ethyl}pyridin-3-amine
70. N-{2-[1-(dipyridin-3-ylamino)ethyl]biphenyl-4-yl}methanesulfonamide
71. N-[1-(4-fluorobiphenyl-2-yl)ethyl]-N-pyridin-3-ylpyridin-3-amine
72. N-[1-(3-chlorobiphenyl-2-yl)ethyl]-N-pyridin-3-ylpyridin-3-amine
73. N-{2-[1-(dipyridin-3-ylamino)ethyl]biphenyl-3-yl}methanesulfonamide
74. N-{1-[2-(3,5-dimethyl-1H-pyrazol4-yl)phenyl]ethyl}-N-pyridin-3-ylpyridin-3-amine
75. N-{1-[2-(1,3-benzodioxol-5-yl)pbenyl]ethyl}-N-pyridin-3-ylpyridin-3-amine
76. N-{1-[2-(2,3-dihydro-1,4-benzodioxin-6-yl)phenyl]ethyl}-N-pyridin-3-ylpyridin-3-amine
77. N-{1-[2-(1-methyl-1H-indol-5-yl)phenyl]ethyl}-N-pyridin-3-ylpyridin-3-amine
78. N-[1-(2-cyclohex-1-en-1-ylphenyl)ethyl]-N-pyridin-3-ylpyridin-3-amine
79. N-[1-(2-chlorobiphenyl-2-yl)ethyl]-N-pyridin-3-ylpyridin-3-amine
80. 2-[1-(dipyridin-3-ylamino)ethyl]biphenyl-2-carbonitrile
81. N-(1-{3-[(4-methylpiperazin-1-yl)carbonyl]biphenyl-2-yl}ethyl)-N-pyridin-3-ylpyridin-3-amine
82. N-[1-(2-cyclopropylphenyl)ethyl]-N-pyridin-3-ylpyridin-3-amine
83. N-{1-[2-(2,6-dimethoxypyridin-3-yl)phenyl]ethyl}-N-pyridin-3-ylpyridin-3-amine
84. N-[1-(4-morpholin-4-ylbiphenyl-2-yl)ethyl]-N-pyridin-3-ylpyridin-3-amine 85. N-(1-{2-[6-(4-methylpiperazin-1-yl)pyridin-3-yl]phenyl}ethyl)-N-pyridin-3-ylpyridin-3-amine
86. N-pyridin-3-yl-N-{1-[2'-(trifluoromethoxy)biphenyl-2-yl]ethyl}pyridin-3-amine
87. N-pyridin-3-yl-N-{1-[3'-(trifluoromethoxy)biphenyl-2-yl]ethyl}pyridin-3-amine
88. N-{1-[2-(1-isobutyl-1H-pyrazol-4-yl)phenyl]ethyl}-N-pyridin-3-ylpyridin-3-amine
89. N-{1-[4-(methylsulfonyl)biphenyl-2-yl]ethyl}-N-pyridin-3-ylpyridin-3-amine
90. N-pyridin-3-yl-N-{1-[4-(trifluoromethyl)biphenyl-2-yl]ethyl}pyridin-3-amine
91. 2-[1-(dipyridin-3-ylamino)ethyl]-N,N-dimethylbiphenyl-3-carboxamide
92. N-[1-(4-fluoro-2-methylbiphenyl-2-yl)ethyl]-N-pyridin-3-ylpyridin-3-amine
93. N-[1-(3-fluoro-4-methoxybiphenyl-2-yl)ethyl]-N-pyridin-3-ylpyridin-3-amine
94. 2'-[1-(dipyridin-3-ylamino)ethyl]-N,N-dimethylbiphenyl-4-carboxamide
95. 2'-[1-(dipyridin-3-ylamino)ethyl]-4-fluorobiphenyl-3-carbonitrile
96. N-[1-(3,5-dichlorobiphenyl-2-yl)ethyl]-N-pyridin-3-ylpyridin-3-amine
97. N-[1-(3-methoxybiphenyl-2-yl)ethyl]-N-pyridin-3-ylpyridin-3-amine
98. N-[1-(2-methoxybiphenyl-2-yl)ethyl]-N-pyridin-3-ylpyridin-3-amine
99. N-[1-(3,4-dimethoxybiphenyl-2-yl)ethyl]-N-pyridin-3-ylpyridin-3-amine
100. N-{1-[2-(3,5-dimethylisoxazol-4-yl)phenyl]ethyl}-N-pyridin-3-ylpyridin-3-amine
101. N-cyclopropyl-2-[1-(dipyridin-3-ylamino)ethyl]biphenyl-3-carboxamide
102. N-pyridin-3-yl-N-{1-[4-(pyrrolidin-1-ylsulfonyl)biphenyl-2-yl]ethyl}pyridin-3-amine
103. 2-[1-(dipyridin-3-ylamino)ethyl]-N,N-diethylbiphenyl-3-carboxamide
104. N-{1-[2-(6-chloropyridin-3-yl)phenyl]ethyl}-N-pyridin-3-ylpyridin-3-amine
105. N-[1-(4-methoxy-3,5-dimethylbiphenyl-2-yl)ethyl]-N-pyridin-3-ylpyridin-3-amine
106. N-pyridin-3-yl-N-{1-[2-(1,3,5-trimethyl-1H-pyrazol-4-yl)phenyl]ethyl}pyridin-3-amine
107. N-{1-[2-fluoro-4-(trifluorometbyl)biphenyl-2-yl]ethyl}-N-pyridin-3-ylpyridin-3-amine
108. 2-[1-(dipyridin-3-ylamino)ethyl]biphenyl-4-carboxamide
109. 2-[1-(dipyridin-3-ylamino)ethyl]-N-methylbiphenyl4-carboxamide
110. N-cyclopropyl-2-[1-(dipyridin-3-ylamino)ethyl]biphenyl-4-carboxamide
111. N-{1-[4-(morpholin-4-ylcarbonyl)biphenyl-2-yl]ethyl}-N-pyridin-3-ylpyridin-3-amine
112. 2-[1-(dipyridin-3-ylamino)ethyl]biphenyl-3-carboxamide
113. 5-{2-[1-(dipyridin-3-ylamino)ethyl]phenyl}pyridin-2-amine
114. N-{[2-(1,1-dioxido-2,3-dihydro-4H-1,4-benzothiazin-4-yl)pyridin-3-yl]methyl}-3-(methylsulfonyl)-N-[3-(methylsulfonyl)phenyl]aniline
115. 3-({bis[3-(methylsulfonyl)phenyl]amino}methyl)-N-[2-(methylthio)phenyl]pyridin-2-amine
116. 3-({bis[3-(methylsulfonyl)phenyl]amino}methyl)-N-[2-(methylsulfonyl)phenyl]pyridin-2-amine
117. N-[(2-chloropyridin-3-yl)methyl]-6-methoxy-N-[3-(methylthio)phenyl]pyridin-3-amine
118. 1-(3-{[(6-methoxypyridin-3-yl)(pyridin-3-yl)amino]methyl}pyridin-2-yl)-1,3-dihydro-2H-benzimidazol-2-one Structures of the compounds listed above are shown below:

1.

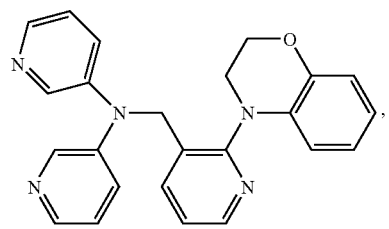

2.

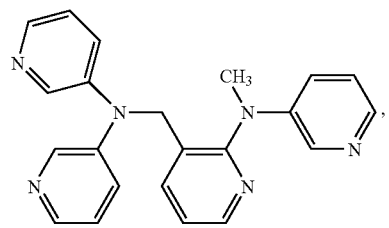

3.

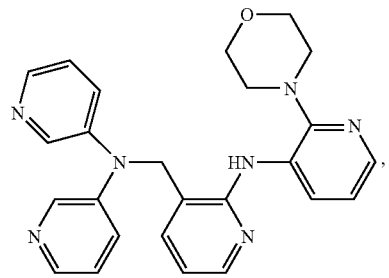

4.

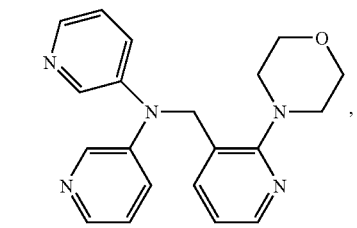

5.

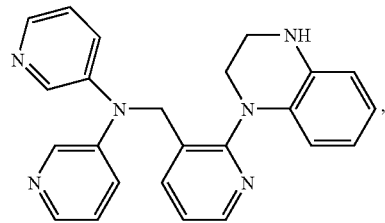

6.

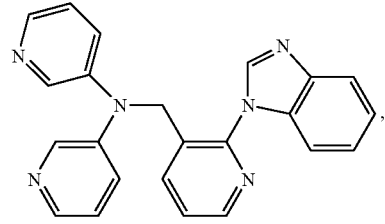

7.
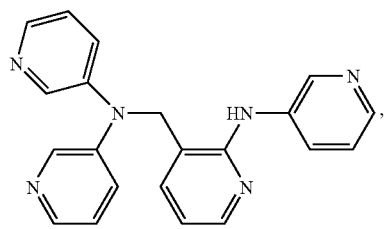
8.
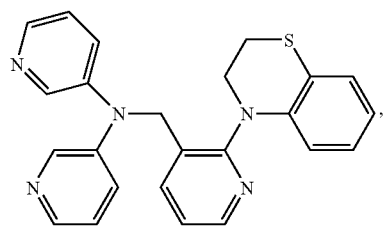
9.
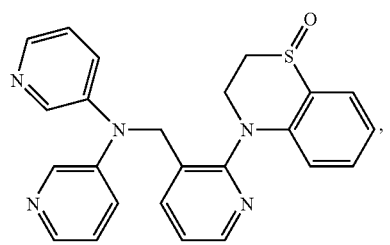
10.
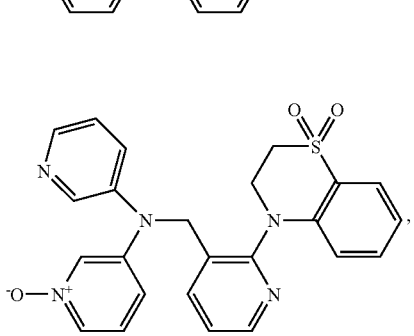
11.
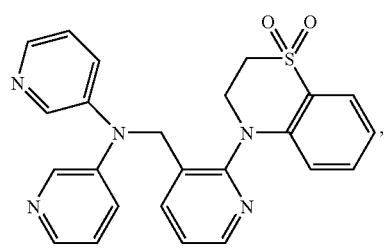
12.
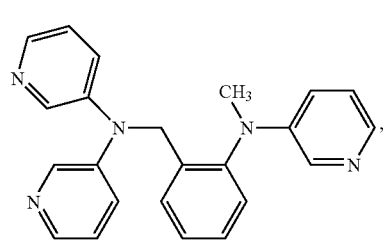
13.
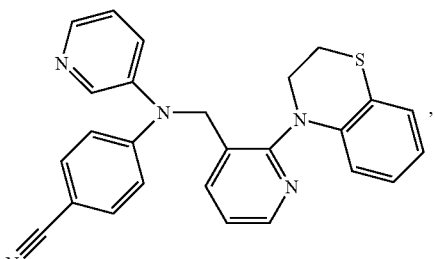
14.
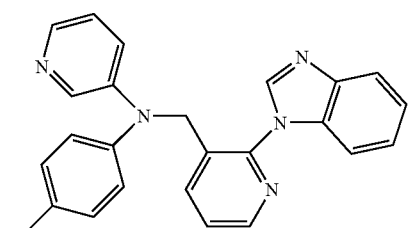
15.
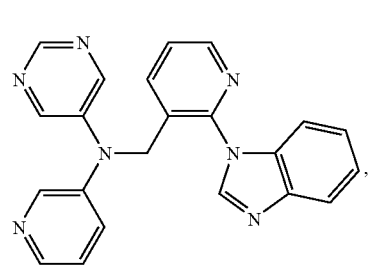
16.
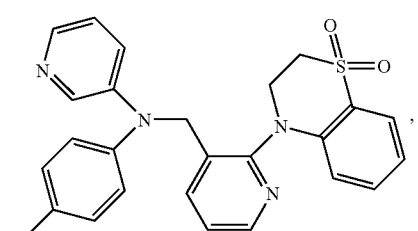
17.
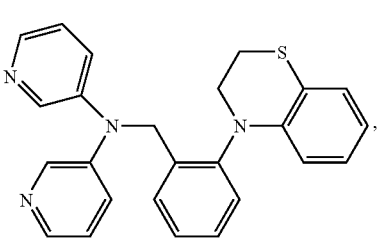
18.
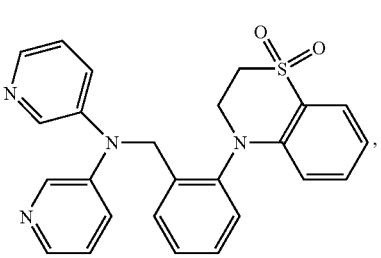

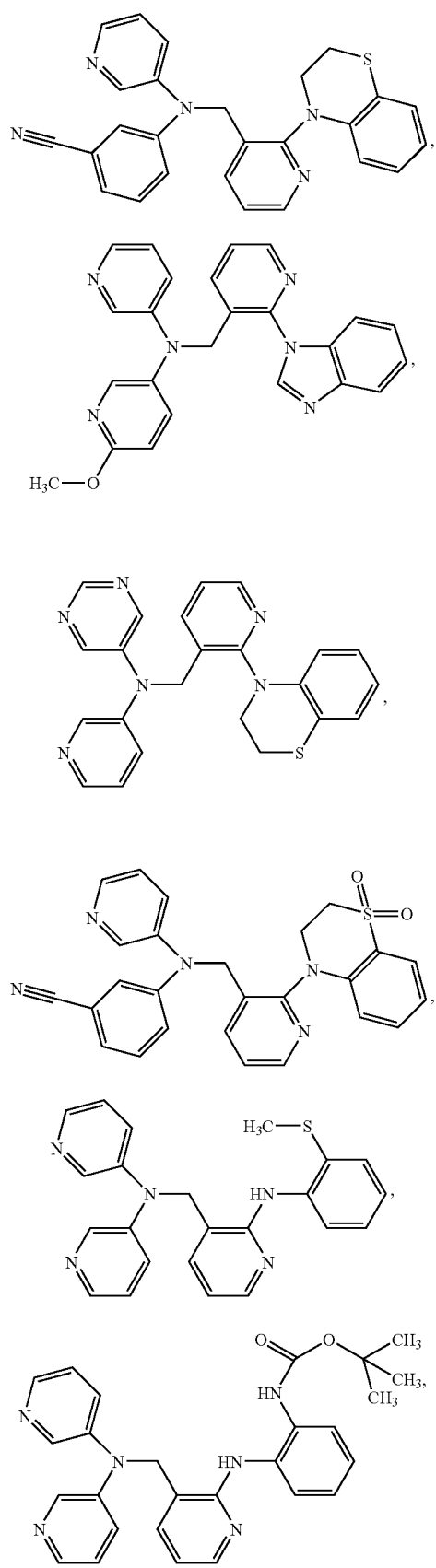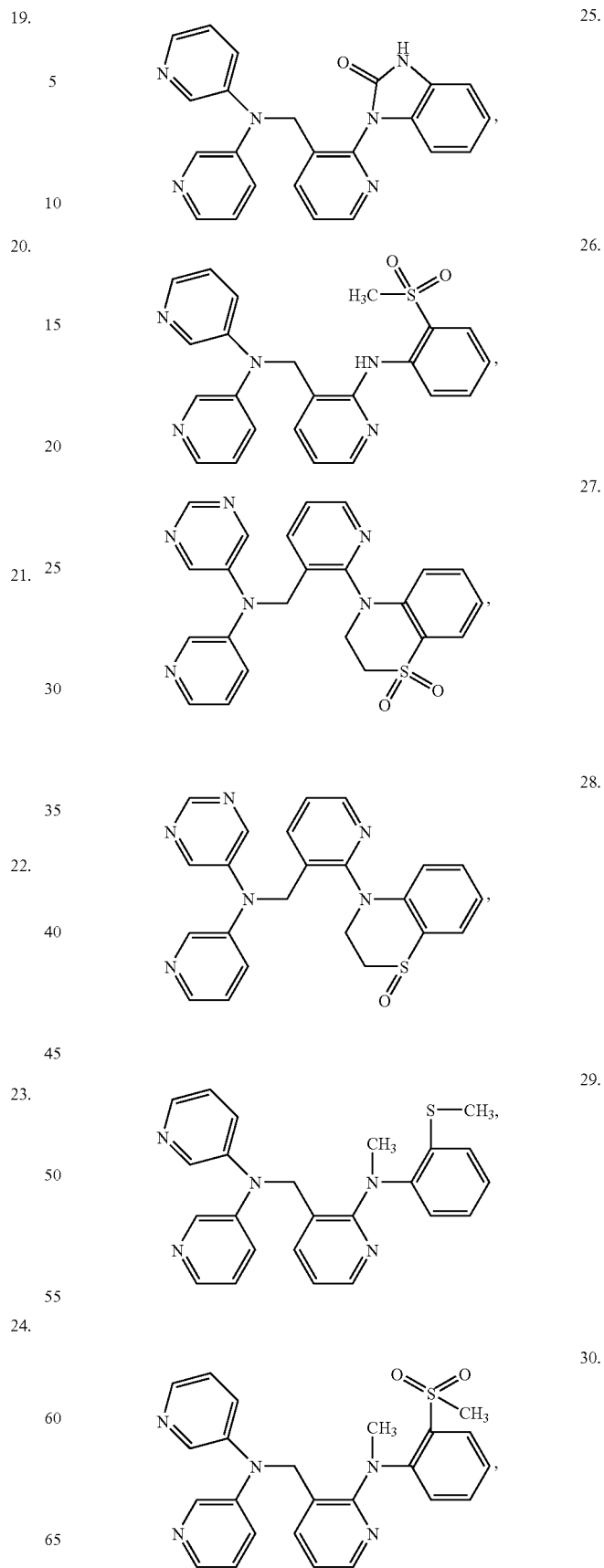

-continued

43.
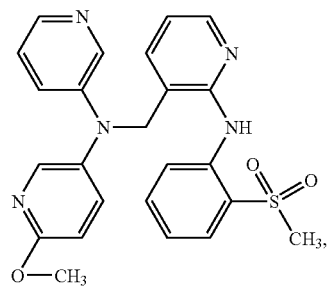
44.
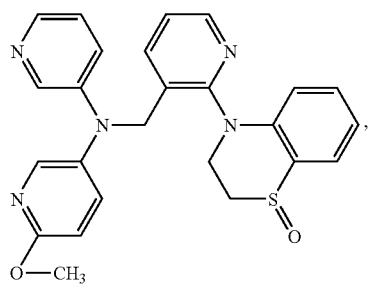
45.
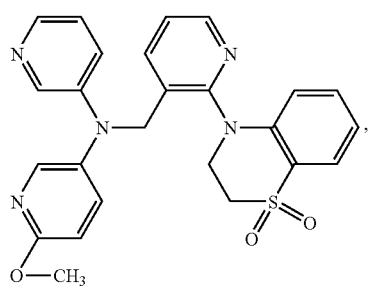
46.
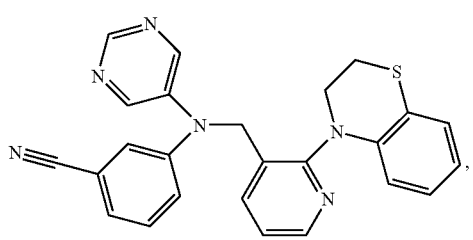
47.
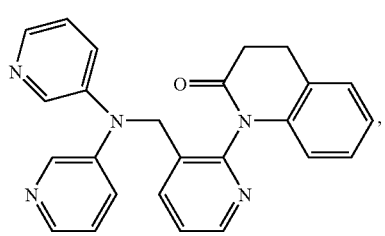
48.
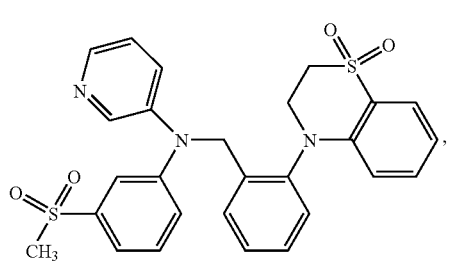
49.
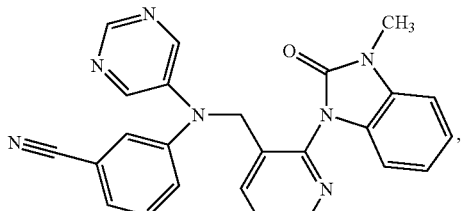
50.
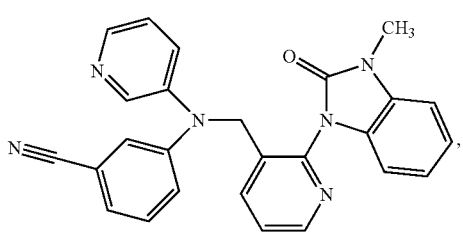
51.
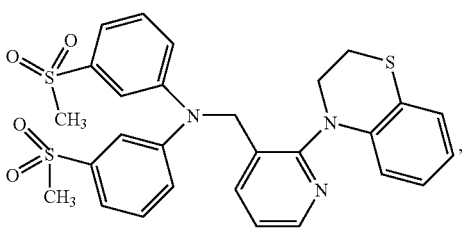
52.
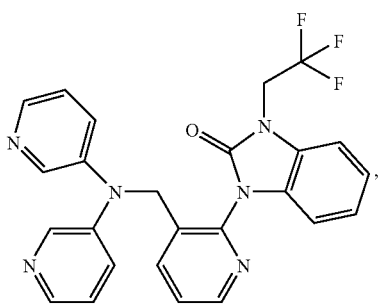
53.
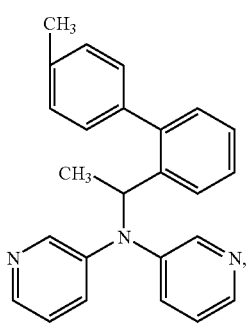
54.
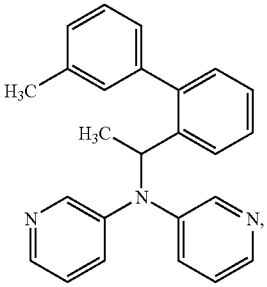

-continued 55.
56.
57.
58.
59.
60.
61.
62.
63.
64.

65. 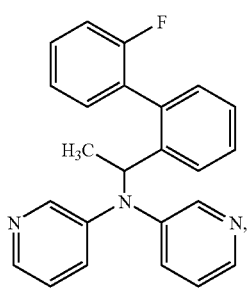
66. 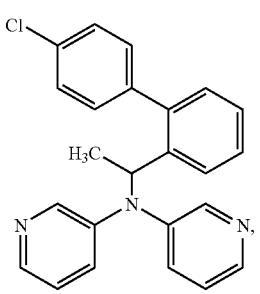
67. 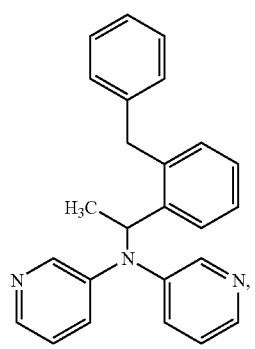
68. 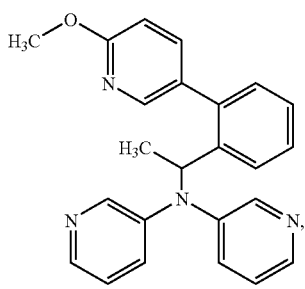
69. 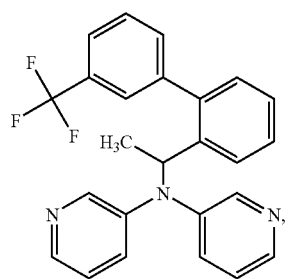
70. 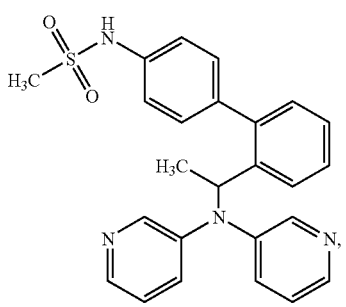
71. 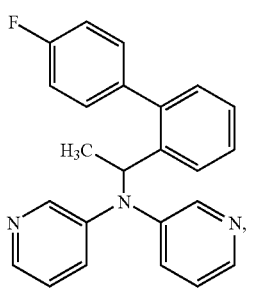
72. 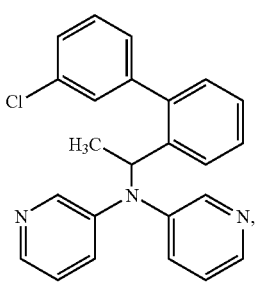
73. 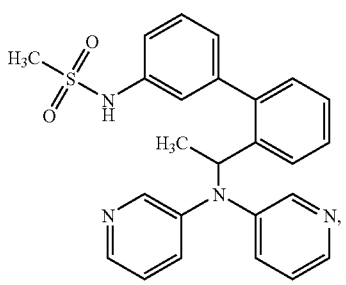
74. 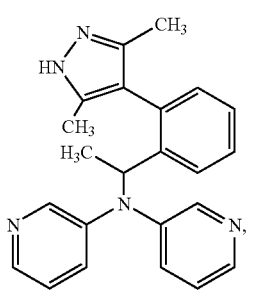

-continued 75.
76.
77.
78.
79.
80.
81.
82.
83.
84.

85.
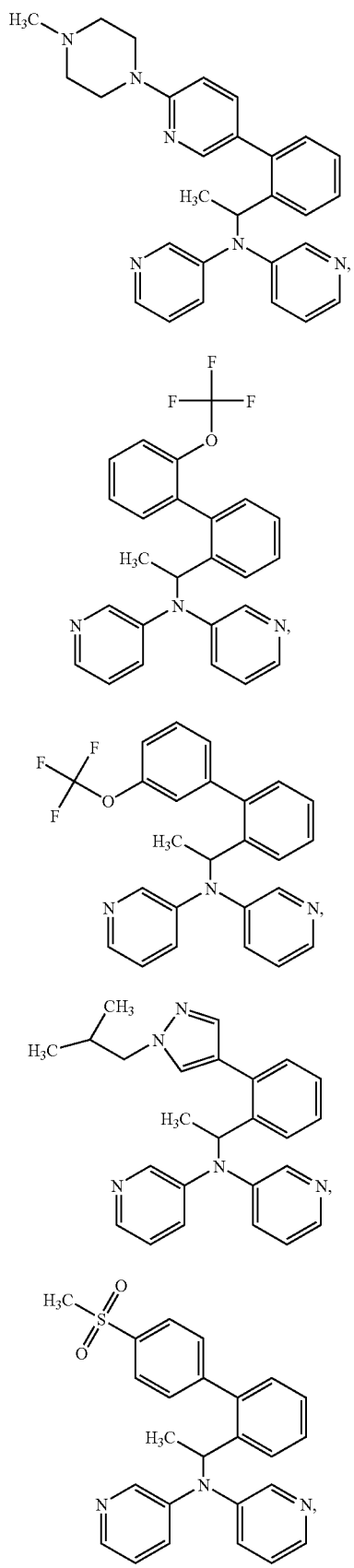
86.
87.
88.
89.
90.
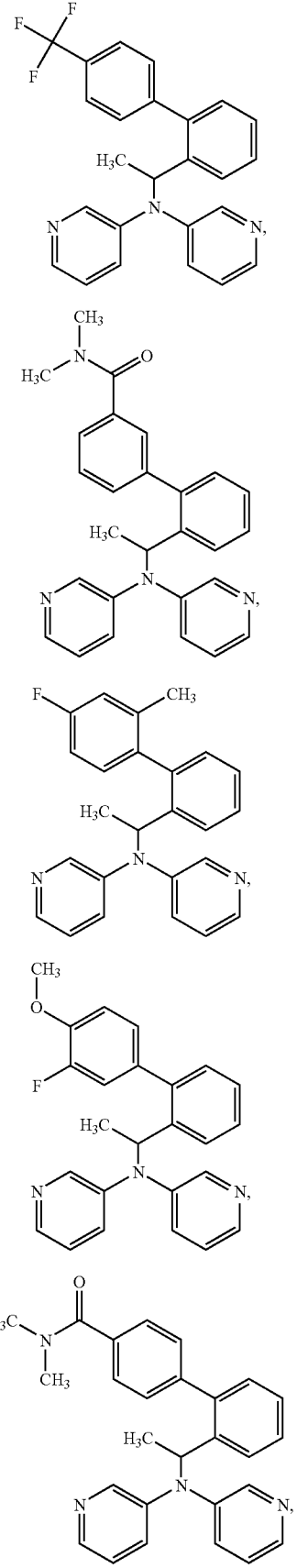
91.
92.
93.
94.

95.
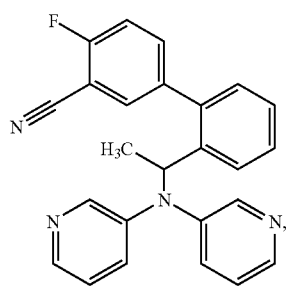
96.
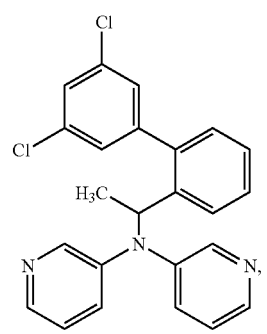
97.
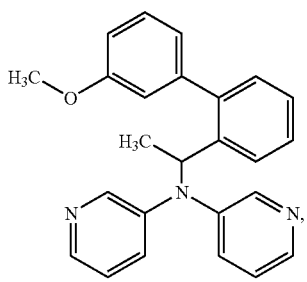
98.
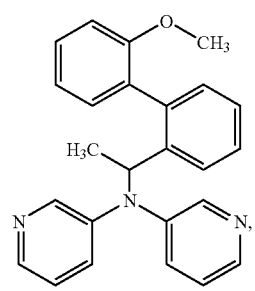
99.
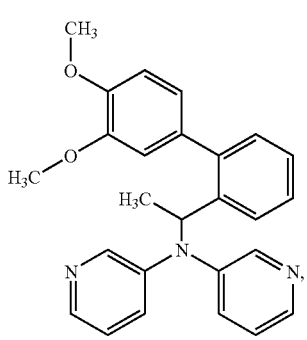
100.
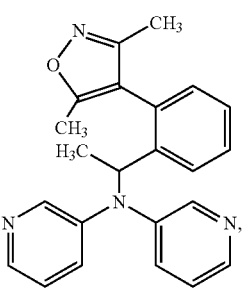
101.
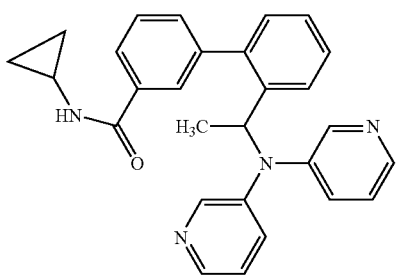
102.
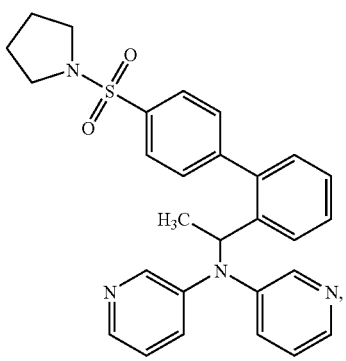
103.
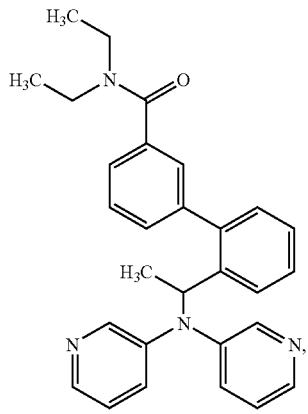
104.

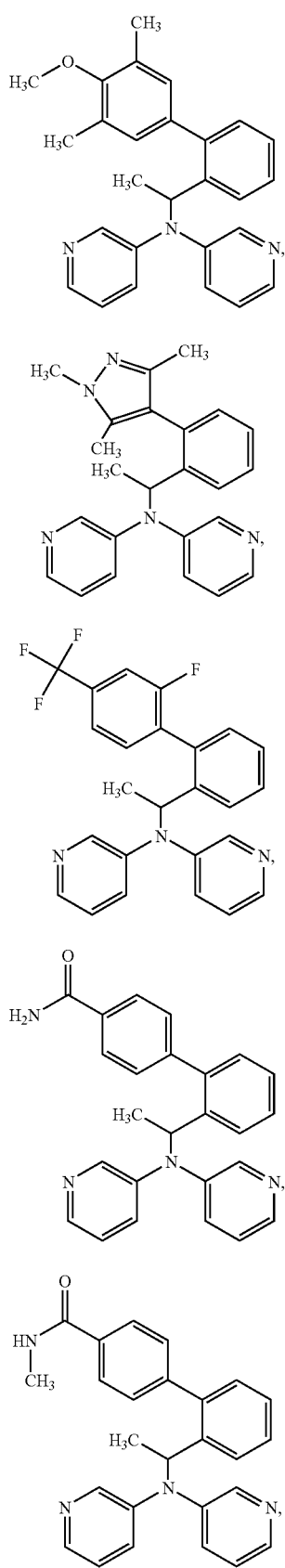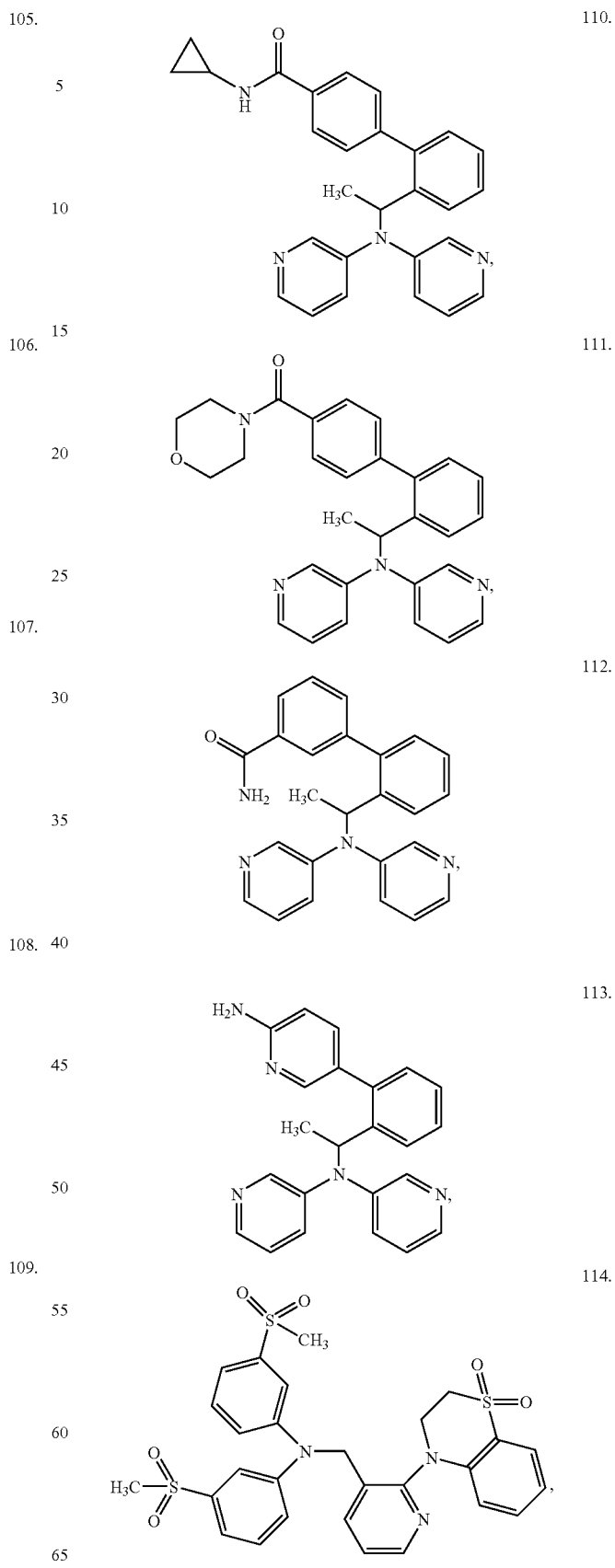

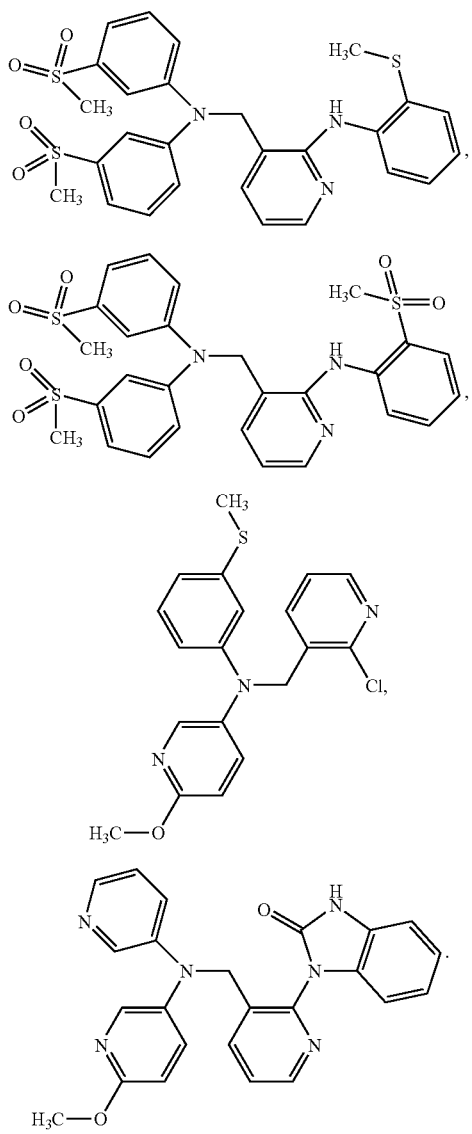

The compounds of the present invention may have chiral centers, e.g. one chiral center (providing for two stereoisomers, (R) and (S)), or two chiral centers (providing for up to four stereoisomers, (R,R), (S,S), (R,S), and (S,R)). This invention includes all of the optical isomers and mixtures thereof. Unless specifically mentioned otherwise, reference to one isomer applies to any of the possible isomers. Whenever the isomeric composition is unspecified, all possible isomers are included.

Tautomers of compounds defined in Formula I are also included within the scope of the present invention. For example, compounds including carbonyl —CH$_2$C(O)— groups (keto forms) may undergo tautomerism to form hydroxyl —CH=C(OH)— groups (enol forms). Both keto and enol forms are included within the scope of the present invention.

In addition compounds with carbon-carbon double bonds may occur in Z- and E-forms with all isomeric forms of the compounds being included in the present invention.

The compounds of the invention may exist as atropisomers, i.e., chiral rotational isomers. The invention encompasses the racemic and the resolved atropisomers.

The above-listed compounds are active in one or more of the assays for Kv1.5 described below.

Another embodiment of the invention is a method of treating or preventing a condition in a mammal, the treatment or prevention of which is effected or facilitated by K$_v$1.5 inhibition, which comprises administering an amount of a compound of Formula I that is effective at inhibiting K$_v$1.5.

A preferred embodiment is a method of treating or preventing cardiac arrhythmias, e.g. atrial fibrillation, atrial flutter, atrial arrhythmia, and supraventricular tachycardia, in a mammal, which comprises administering a therapeutically effective amount of a compound of Formula I.

Another preferred embodiment is a method of preventing thromboembolic events, such as stroke.

Another preferred embodiment is a method of preventing congestive heart failure.

Another preferred embodiment is a method for inducing in a patient having atrial fibrillation, a condition of normal sinus rhythm, in which the induced rhythm corresponds to the rhythm that would be considered normal for an individual sharing with the patient similar size and age characteristics, which comprises treating the patient with a compound of the invention.

Another preferred embodiment is a method for treating tachycardia, (i.e., rapid heart rate e.g. 100 beats per minute) in a patient which comprises treating the patient with an anti-tachycardia device (e.g. a defibrillator or a pacemaker) in combination with a compound of claim 1.

The present invention also encompasses a pharmaceutical formulation comprising a pharmaceutically acceptable carrier and the compound of Formula I or a pharmaceutically acceptable crystal form or hydrate thereof. A preferred embodiment is a pharmaceutical composition of the compound of Formula I, comprising, in addition, a second agent.

List of abbreviations:
AAS atomic absorption spectroscopy
AF atrial fibrillation
ACE angiotensin converting enzyme
CHO Chinese hamster ovary
DMSO dimethylsulfoxide
dppf 1,1'-(diphenylphosphino)ferrocene
EDTA ethylenediaminetetraacetic acid
EGTA ethylenebis(oxyethylenenitrilo)tetraacetic acid
FAAS flame atomic absorption spetroscopy
FBS fetal bovine serum
HBSS Hank's balanced salt solution
HEPES N-2-hydroxyethylpiperazine-N'-2-ethanesulphonic acid
LDA lithium diisopropylamide
LYS lysate
NMR nuclear magnetic resonance
NSAID non-steroidal antiinflarmnatory drug
PBS phosphate-buffered saline
RMS root mean square deviation
RT room temperature
THF tetrahydrofuiran
XANTPHOS 9,9-dimethyl-4,5-bis(diphenylphosphino)xanthene As used herein except where noted, "alky" is intended to include both branched- and straight-chain saturated aliphatic hydrocarbon groups, including all isomers, having the specified number of carbon atoms. Commonly used abbreviations for alkyl groups are used throughout the specification, e.g. methyl may be represented by "Me" or CH$_3$, ethyl may be represented by "Et" or CH$_2$CH$_3$, propyl may be represented by "Pr" or CH$_2$CH$_2$CH$_3$, butyl may be represented by "Bu" or CH$_2$CH$_2$CH$_2$CH$_3$, etc. "C$_{1-6}$ alky" (or "C$_1$-C$_6$ alkyl") for example, means linear or branched chain alkyl groups, including all isomers, having the specified number of carbon atoms. $C_{1-6}$ alkyl includes all of the hexyl alkyl and pentyl alkyl isomers as well as n-, iso-, sec- and t-butyl, n- and isopropyl, ethyl and methyl. "$C_{1-4}$ alkyl" means n-, iso-, sec- and t-butyl, n- and isopropyl, ethyl and methyl. The term "alkoxy" represents a linear or branched alkyl group of indicated number of carbon atoms attached through an oxygen bridge.

The term "alkenyl" includes both branched and straight chain unsaturated hydrocarbon groups containing at least two carbon atoms joined by a double bond. The alkene ethylene is represented, for example, by "$CH_2CH_2$" or alternatively, by "$H_2C=CH_2$". "$C_{2-5}$ alkenyl" (or "$C_2$-$C_5$ alkenyl") for example, means linear or branched chain alkenyl groups having from 2 to 5 carbon atoms and includes all of the pentenyl isomers as well as 1-butenyl, 2-butenyl, 3-butenyl, 1-propenyl, 2-propenyl, and ethenyl (or ethylenyl). Similar terms such as "$C_{2-3}$ alkenyl" have an analogous meaning.

The term "alkynyl" includes both branched and straight chain unsaturated hydrocarbon groups containing at least two carbon atoms joined by a triple bond. The alkyne acetlyene is represented, for example, by "CHCH" or alternatively, by "HC≡CH". "$C_{2-5}$ alkynyl" (or "$C_2$-$C_5$ alkynyl") for example, means linear or branched chain alkynyl groups having from 2 to 5 carbon atoms and includes all of the pentynyl isomers as well as 1-butynyl, 2-butynyl, 3-butynyl, 1-propynyl, 2-propynyl, and ethynyl (or acetylenyl). Similar terms such as "$C_{2-3}$ alkynyl" have an analogous meaning.

Unless otherwise specifically noted as only "unsubstituted" or only "substituted", alkyl, alkenyl and alkynyl groups are unsubstituted or substituted with 1 to 3 substituents on each carbon atom, with halo, $C_1$-$C_{20}$ alkyl, $CF_3$, $NH_2$, —$NH(C_1$-$C_6$ alkyl), —$N(C_1$-$C_6$ alkyl)$_2$, $NO_2$, oxo, CN, $N_3$, —OH, —$O(C_1$-$C_6$ alkyl), $C_3$-$C_{10}$ cycloalkyl, $C_2$-$C_6$ alkenyl, $C_2$-$C_6$ alkynyl, $(C_0$-$C_6$ alkyl) $S(O)_{0-2}$—, $(C_0$-$C_6$ alkyl)$S(O)_{0-2}$ $(C_0$-$C_6$ alkyl)-, $(C_0$-$C_6$ alkyl)$C(O)NH$—, $H_2N$—$C(NH)$—, —$O(C_1$-$C_6$ alkyl)$CF_3$, $(C_0$-$C_6$ alkyl)$C(O)$—, $(C_0$-$C_6$ alkyl)$OC(O)$—, $(C_0$-$C_6$ alkyl)$O(C_1$-$C_6$ alkyl)-, $(C_0$-$C_6$ alkyl)$C(O)_{1-2}(C_0$-$C_6$ alkyl)-, $(C_0$-$C_6$ alkyl)$OC(O)NH$—, aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl.

The term "$C_0$" as employed in expressions such as "$C_{0-6}$ alkyl" means a direct covalent bond. Similarly, when an integer defining the presence of a certain number of atoms in a group is equal to zero, it means that the atoms adjacent thereto are connected directly by a bond. For example, in the structure

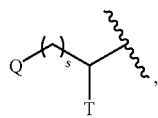

wherein s is an integer equal to zero, 1 or 2, the structure is

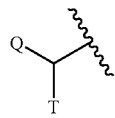

when s is zero.

The term "$C_{3-8}$ cycloalkyl" (or "$C_3$-$C_8$ cycloalkyl") means a cyclic ring of an alkane having three to eight total carbon atoms (i.e., cyclopropyl, cyclobutyl, cyclopentyl, cyclohexyl, cycloheptyl, or cyclooctyl). The terms "$C_{3-7}$ cycloalkyl", "$C_{3-6}$ cycloalkyl", "$C_{5-7}$ cycloalkyl" and the like have analogous meanings.

The term "unsaturated", when used with reference to a ring, means a ring having the maximum number of non-cumulative ring double bonds. The term "saturated", when used with reference to a ring, means a ring having either partial (at least one ring double bond but less than the maximal number of ring double bonds) or complete (having no ring double bonds) saturation. the term "halogen" (or "halo") refers to fluorine, chlorine, bromine and iodine (alternatively referred to as fluoro (F), chloro (Cl), bromo (Br), and iodo (I)).

The term "$C_{1-6}$ haloalkyl" (which may alternatively be referred to as "$C_1$-$C_6$ haloalkyl" or "halogenated $C_1$-$C_6$ alkyl") means a $C_1$ to $C_6$ linear or branched alkyl group as defined above with one or more halogen substituents. The term "$C_{1-4}$ haloalkyl" has an analogous meaning. The term "$C_{1-6}$ fluoroalkyl" has an analogous meaning except that the halogen substituents are restricted to fluoro. Suitable fluoroalkyls include the series $(CH_2)_{0-4}CF_3$ (i.e., trifluoromethyl, 2,2,2-trifluoroethyl, 3,3,3-trifluoro-n-propyl, etc.).

The term "carbocycle" (and variations thereof such as "carbocyclic" or "carbocyclyl") as used herein, unless otherwise indicated, refers to (i) a $C_3$ to $C_8$ monocyclic, saturated or unsaturated ring or (ii) a $C_7$ to $C_{12}$ bicyclic saturated or unsaturated ring system. Each ring in (ii) is either independent of, or fused to, the other ring, and each ring is saturated or unsaturated. The carbocycle may be attached to the rest of the molecule at any carbon atom which results in a stable compound. The fused bicyclic carbocycles are a subset of the carbocycles; i.e., the term "fused bicyclic carbocycle" generally refers to a $C_7$ to $C_{10}$ bicyclic ring system in which each ring is saturated or unsaturated and two adjacent carbon atoms are shared by each of the rings in the ring system. A fused bicyclic carbocycle in which one ring is saturated and the other is saturated is a saturated bicyclic ring system. A fused bicyclic carbocycle in which one ring is benzene and the other is saturated is an unsaturated bicyclic ring system. A fused bicyclic carbocycle in which one ring is benzene and the other is unsaturated is an unsaturated ring system. Saturated carbocyclic rings are also referred to as cycloalkyl rings, e.g., cyclopropyl, cyclobutyl, etc. Unless otherwise noted, carbocycle is unsubstituted or substituted with $C_{1-6}$ alkyl, $C_{1-6}$ alkenyl, $C_{1-6}$ alkynyl, aryl, halogen, $NH_2$ or OH. A subset of the fused bicyclic carbocycles are those bicyclic carbocycles in which one ring is a benzene ring and the other ring is saturated or unsaturated, with attachment via any carbon atom that results in a stable compound. Representative examples of this subset include the following:

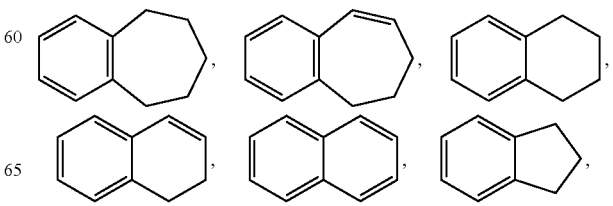

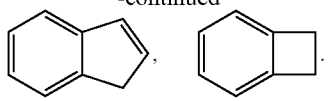

The term "aryl" refers to aromatic mono- and poly-carbocyclic ring systems, wherein the individual carbocyclic rings in the polyring systems are fused or attached to each other via a single bond. Suitable aryl groups include phenyl, naphthyl, and biphenylenyl.

The term "heterocycle" (and variations thereof such as "heterocyclic" or "heterocyclyl") broadly refers to (i) a stable 4- to 8-membered, saturated or unsaturated monocyclic ring, or (ii) a stable 7- to 12-membered bicyclic ring system, wherein each ring in (ii) is bridged, fused, or spirocyclic, and independently saturated or unsatrurated, and the monocyclic ring or bicyclic ring system contains one or more heteroatoms (e.g., from 1 to 6 heteroatoms, or from 1 to 4 heteroatoms) selected from N, O and S and a balance of carbon atoms (the monocyclic ring typically contains at least one carbon atom and the ring systems typically contain at least two carbon atoms); and wherein any one or more of the nitrogen and sulfur heteroatoms is optionally oxidized, and any one or more of the nitrogen heteroatoms is optionally quaternized. The heterocyclic ring may be attached at any heteroatom or carbon atom, provided that attachment results in the creation of a stable structure. When the heterocyclic ring has substituents, it is understood that the substituents may be attached to any atom in the ring, whether a heteroatom or a carbon atom, provided that a stable chemical structure results.

Unless otherwise specifically noted as only "unsubstituted" or only "substituted", cycloalkyl, aryl and heterocycle groups are unsubstituted or substituted. As used herein, the terms "substituted $C_3$-$C_{10}$ cycloalkyl", "substituted aryl" and "substituted heterocycle" are intended to include the cyclic group containing from 1 to 4 substituents in addition to the point of attachment to the rest of the compound. Preferably, the substituents are selected from the group which includes, but is not limited to, halo, $C_1$-$C_{20}$ alkyl, $CF_3$, $NH_2$, —NH($C_1$-$C_6$ alkyl), —N($C_1$-$C_6$ alkyl)$_2$, $NO_2$, oxo, CN, $N_3$, —OH, —O($C_1$-$C_6$ alkyl), $C_3$-$C_{10}$ cycloalkyl, $C_2$-$C_6$ alkenyl, $C_2$-$C_6$ alkynyl, ($C_0$-$C_6$ alkyl)-S(O)$_{0-2}$—, aryl-S(O)$_{0-2}$—, ($C_0$-$C_6$ alkyl)S(O)$_{0-2}$($C_0$-$C_6$ alkyl)-, ($C_0$-$C_6$ alkyl)C(O)NH—, $H_2$N—C(NH)—, —O($C_1$-$C_6$ alkyl)$CF_3$, ($C_0$-$C_6$ alkyl)C(O)—, ($C_0$-$C_6$ alkyl)OC(O)—, ($C_0$-$C_6$alkyl)O($C_1$-$C_6$ alkyl)-, ($C_0$-$C_6$ alkyl)C(O)$_{1-2}$($C_0$-$C_6$ alkyl)-, ($C_0$-$C_6$ alkyl)OC(O)NH—, aryl, aralkyl, heteroaryl, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl.

Saturated heterocyclics form a subset of the heterocycles, i.e., the term "saturated heterocyclic" generally refers to a heterocycle as defined above in which the ring system (whether mono- or poly-cyclic) is saturated. The term "saturated heterocyclic ring" refers to a 4- to 8-membered saturated monocyclic ring or a stable 7- to 12-membered bicyclic ring system which consists of carbon atoms and one or more heteroatoms selected from N, O and S. Representative examples include piperidinyl, piperazinyl, azepanyl, pyrrolidinyl, pyrazolidinyl, imidazolidinyl, oxazolidinyl, isoxazolidinyl, morpholinyl, thiomorpholinyl, thiazolidinyl, isothiazolidinyl, indolyl, tetrahydroquinolinyl, benzoxazinyl, tetrahydroquinoxalinyl, benzodioxinyl, diazaspiro[4.4]nonanyl, piperazinone, and tetrahydroftryl (or tetrahydrofuranyl).

Heteroaromatics form another subset of the heterocycles; i.e., the term "heteroaromatic" (alternatively "heteroaryl") generally refers to a heterocycle as defined above in which the entire ring system (whether mono- or poly-cyclic) is an aromatic ring system. The term "heteroaromatic ring" refers a 5- or 6-membered monocyclic aromatic ring or a 7- to 12-membered bicyclic which consists of carbon atoms and one or more heteroatoms selected from N, O and S. In the case of substituted heteroaryl rings containing at least one nitrogen atom (e.g., pyridine), such substitutions can be those resulting in N-oxide formation. Representative examples of heteroaromatic rings include pyridyl, pyrrolyl, pyrazinyl, pyrimidinyl, pyridazinyl, thienyl (or thiophenyl), thiazolyl, furanyl, imidazolyl, pyrazolyl, triazolyl, tetrazolyl, oxazolyl, isooxazolyl, oxadiazolyl, thiazolyl, isothiazolyl, and thiadiazolyl.

Representative examples of bicyclic heterocycles include benzotriazolyl, indolyl, isoindolyl, indazolyl, indolinyl, isoindolinyl, quinoxalinyl, quinazolinyl, cinnolinyl, chromanyl, isochromanyl, tetrahydroquinolinyl, quinolinyl, tetrahydroisoquinolinyl, isoquinolinyl, pyridinone, 2,3-dihydrobenzofuranyl, 2,3-dihydrobenzo-1,4-dioxinyl (i.e., 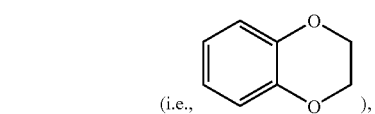 ), imidazo(2,1-b)(1,3)thiazole, (i.e., 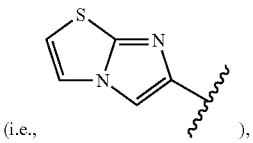 ), and benzo-1,3-dioxolyl (i.e., 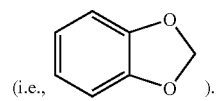 ).

In certain contexts herein,

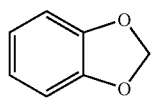

is alternatively referred to as phenyl having as a substituent methylenedioxy attached to two adjacent carbon atoms.

Unless expressly stated to the contrary, a "saturated" ring is a partially or completely saturated ring. For example, a "saturated monocyclic $C_6$ carbocycle" refers to cyclohexane.

Unless expressly stated to the contrary, all ranges cited herein are inclusive. For example, a heterocycle described as containing from "1 to 4 heteroatoms" means the heterocycle can contain 1, 2, 3 or 4 heteroatoms.

When any variable occurs more than one time in any constituent or in any formula depicting and describing compounds of the invention, its definition on each occurrence is independent of its definition at every other occurrence. Also, combinations of substituents and/or variables are permissible only if such combinations result in stable compounds.

The term "substituted" (e.g., as in "aryl which is optionally substituted with one or more substituents . . . ") includes mono- and poly-substitution by a named substituent to the extent such single and multiple substitution (including multiple substitution at the same site) is chemically allowed.

In compounds of the invention having N-oxide moieties, e.g., pyridyl N-oxide moieties, the N-oxide moiety is structurally depicted using using conventional representations. For example, a pyridyl-N-oxide portion is structurally depicted as

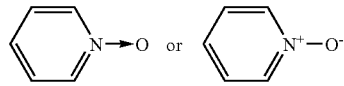

which have equivalent meanings.

For variable definitions containing terms having repeated terms, e.g., $(CR^iR^j)_r$, where r is the integer 2, $R^i$ is a defined variable, and $R^j$ is a defined variable, the value of $R^i$ may differ in each instance in which it occurs, and the value of $R^j$ may differ in each instance in which it occurs. For example, if $R^i$ and $R^j$ are independently selected from the group consisting of methyl, ethyl, propyl and butyl, then $(CR^iR^j)_2$ can be

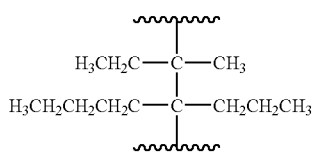

Pharmaceutically acceptable salts include both the metallic (inorganic) salts and organic salts; a list of which is given in *Remington's Pharmaceutical Sciences*, 17th Edition, pg. 1418 (1985). It is well known to one skilled in the art that an appropriate salt form is chosen based on physical and chemical stability, flowability, hydro-scopicity and solubility. As will be understood by those skilled in the art, pharmaceutically acceptable salts include, but are not limited to salts of inorganic acids such as hydrochloride, sulfate, phosphate, diphosphate, hydrobromide, and nitrate or salts of an organic acid such as malate, maleate, fumarate, tartrate, succinate, citrate, acetate, lactate, methanesulfonate, p-toluenesulfonate or palmoate, salicylate and stearate. Similarly pharmaceutically acceptable cations include, but are not limited to sodium, potassium, calcium, aluminum, lithium and ammonium (especially ammonium salts with secondary amines). Preferred salts of this invention for the reasons cited above include potassium, sodium, calcium and ammonium salts. Also included within the scope of this invention are crystal forms, hydrates and solvates of the compounds of Formula I.

Methods for preparing the compounds of this invention are illustrated in the following schemes and examples. Other synthetic protocols will be readily apparent to those skilled in the art. The schemes and examples illustrate the preparation of the compounds of Formula I and as such are not to be considered as limiting the invention set forth in the claims appended hereto. Examples described hereinafter comprise a further embodiment of the present invention.

SCHEME 1

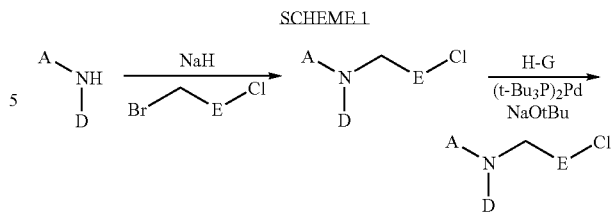

Variables A, D, E and G have their meanings as defined above. N (nitrogen) has its ordinary meaning.

EXAMPLE 1

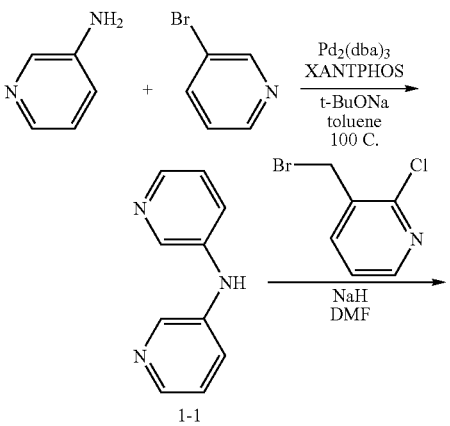

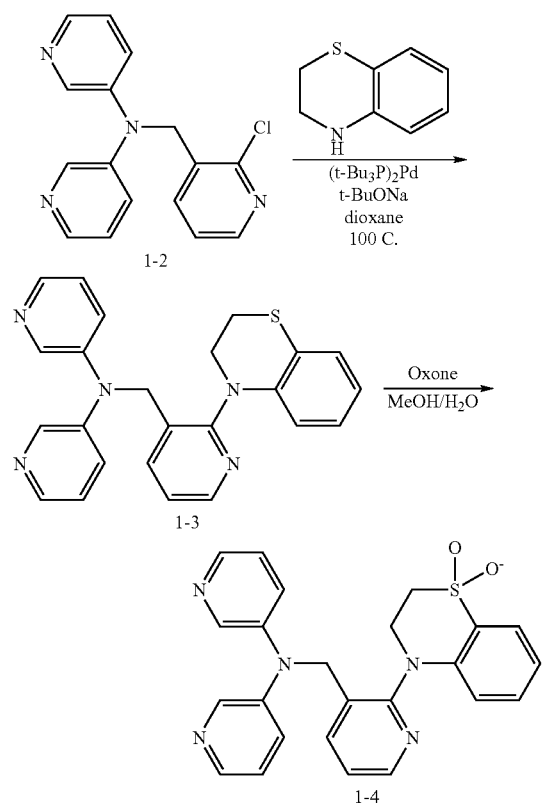

N-{[2-(1,1-dioxido-2,3-dihydro-4H-1,4-benzothi-azin-4-yl)pyridine-3-yl]methyl}-N-pyridin-3-ylpyridin-3-amine (1-4)

Preparation of N-pyridin-3-ylpyridin-3-amine (1-1)

To a solution of 3-bromopyridine (4.75 gm, 30 mmol) and 3-aminopyridine (1.88 gm, 20 mmol) in dry toluene (8 mL) was added sodium t-butoxide (2.3 gm, 24 mmol), tris(dibenylideneacetone) dipalladium(0) (63 mg, 0.069 mmol), and 9,9-dimethyl-4,5-bis(diphenylphosphino)xanthene (XANTPHOS) (183 mg, 0.317 mmol). The vessel was capped with a septum, degassed (3x), and heated at 100 C for ~24 hours. The cooled reaction was diluted with methylene chloride, washed with NaHCO3 solution, water, and the organic layer dried over anhydrous sodium sulfate, filtered and the solvent concentrated to a small volume. Upon addition of diethyl ether and a few drops of methanol the product precipitated. After stirring this mixture for ~15 hours the purified product was isolated by filtration to give 2.89 gm (84% yield) of the title compound.

Preparation of N-[(2-choropyridin-3-yl)methyl]-N-pyridin-3-ylpyridin-3-amine (1-2):

To a solution of N-pyridin-3-ylpyridin-3-amine (510 mg, 3 mmol) in anhydrous DMF (4.5 mL) was added 60% sodium hydride/mineral oil (169 mg, 4.2 mmol). After stirring at ambient temperature for 15 min., 3-(bromomethyl)-2-chloropyridine (677 mg, 3.28 mmol) (preparation described in U.S. Pat. No. 5,739,326) was added neat and the action was stirred for ~2 hours. The reaction was diluted with ethyl acetate, washed with NaHCO3 solution, then water, and the organic layer was dried over anhydrous sodium sulfate, filtered, and the solvent evaporated. The residue was purified by silica gel chromato-graphy eluting with a 20-90% acetonelhexane gradient to give the purified product which upon trituration with diethyl ether gave the title compound as a tan solid (684 mg, 77% yield). 1H-NMR (500 MHz, CDCl$_3$): δ 8.40 (2H, d, J=2.7 Hz), 8.34 (1H, d, J=4.6 Hz), 8.30 (2H, d, J=4.6 Hz), 7.69 (1H, d, J=7.8 Hz), 7.33-7.35 (2H, br d, J=~8.3 Hz), 7.20-7.26 (4H, m), 5.04 (2H, s). m/e (m+1): 297.0

Preparation of N-{[2-(2,3-dihydro-4H-1,4-benzothi-azin-4-yl)pyridine-3-yl]methyl}-N-pyridin-3-ylpyri-din-3-amine (1-3)

To a solution of N-[(2-chloropyridin-3-yl)methyl]-N-pyridin-3-ylpyridin-3-amine (110 mg, 0.37 mmol) and 3,4-dihydro-2H-1,4-benzothiazine (85 mg, 0.56 mmol) (prepared according to procedure described in patent WO 0220498) in dry dioxane (1.25 mnL) was added sodium t-butoxide (48 mg, 0.50 mmol), and bis(tri-t-butylphosphine) palladium(0) (34 mg, 0.066 mmol). The vessel was sealed with a septum cap, degassed (3x), and heated at 100 C for 3 hours. The cooled reaction was diluted with methylene chloride and washed with NaHCO$_3$ solution, and water and the organic layer was dried over anhydrous sodium sulfate, filtered, and the solvent evaporated. The residue was subjected to silica gel chromatography eluting with a 20-90% acetone/hexane gradient to give the title compound as a colorless glass(114 mg, 75% yield). 1H-NMR (500 MHz, CDCl$_3$): δ 8.41 (1H, d, J=4.9 Hz), 8.28 (2H, d, J=3.7 Hz), 8.23 (2H, d, J=4.6 Hz), 7.70 (1H, d, J=6.1 Hz), 7.21-7.26 (4H, m), 7.17 (1H, d, J=3.7 Hz), 7.16 (1H, d, J=4.6 Hz), 7.06 (1H, dd, J=4.9, 7.6 Hz), 6.91 (1H, t, J=7.8 Hz), 6.84 (1H, t, J=7.6 Hz), 6.32 (1H, d, J=8.0 Hz), 4.56 (2H,s), 4.13 (2H, br s), 3.32 (2H, t, J=5.6 Hz). m/e (m+1): 412.2.

Preparation of N-{[2-(1,1-dioxido-2,3-dihydro-4H-1,4-benzothiazin-4-yl)pyridine-3-yl]methyl}-N-pyri-din-3-ylpyridin-3-amine (1-4)

To a solution of: N-{[2-(2,3-dihydro-4H-1,4-benzothi-azin-4-yl)pyridine-3-yl]methyl}-N-pyridin-3-ylpyridin-3-amine (52 mg, 0.126 mmol) in methanol (1.5 mL) and water (1 mL) was added Oxone™ (97 mg, 0.157 mmol). The reaction progress was monitored by LC/MS and after 2 hours the reaction was diluted with water and Na$_2$CO$_3$ solution and the product was extracted into ethyl acetate, the solution dried, filtered, and the solvent evaporated. The residue was purified by chromatography on silica gel eluting with a 20-100% acetone/hexane gradient to give the title compound as a coloress glass. 1H-NMR (500 MHz, CDCl$_3$): δ 8.51 (1H, d, J=3.6 Hz), 8.29 (2H, s), 8.26 (2H, d, J=3.9 Hz), 7.88 (2H, t, J=9.0 Hz), 7.26-7.31 (4H, m), 7.18-7.21 (2H, m), 7.00 (1H, t, J=7.3 Hz), 6.22 (1H, d, J=8.3 Hz), 4.76 (2H, s), 4.38 (2H, br s), 3.57 (2H, t, J=5.8 Hz). m/e (m+1): 444.2.

EXAMPLE 2

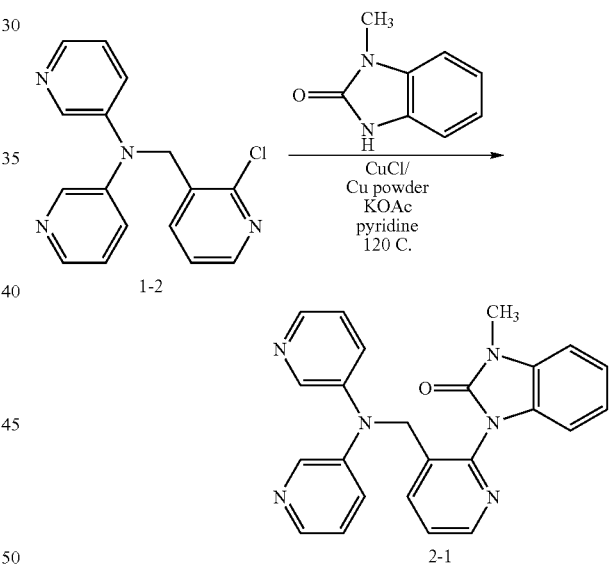

1-{3-[(dipyridin-3-ylamino)methyl]pyridine-2-yl}-3-methyl-1,3-dihydro-2H-benzimidazol-2-one (2-1)

To a solution of N-[(2-chloropyridin-3-yl)methyl]-N-pyridin-3-ylpyridin-3-amine (59 mg, 020 mmol) and 1-methyl-2-benzimidazolinone (45 mg, 0.30 mmol) in dry pyridine (1 mL) was added potassium acetate (51 mg, 0.512 mmol), cuprous chloride (11.6 mg, 0.117 mmol), and copper powder (31 mg, 0.487 mmol). This mixture was sealed and heated at 120 C for 4 days. The cooled reaction was diluted with NaHCO3 solution and the product extracted into methylene chloride. This solution was dried over anhydrous sodium sulfate, filtered, and the solvent evaporated This residue was subjected to chromatography on silica gel eluting with a 20-100% acetone/hexane gradient to give the title compound after trituration with diethyl ether as a white solid.

1H-NMR (500 MHz, CDCl$_3$): δ 8.54 (1H, d, J=3.7 Hz), 8.36 (2H, v br s), 8.25 (2H, v br s), 7.95 (1H, d, J=7.3 Hz), 7.33-7.38 (3H, m), 7.27(1H, m), 7.18-7.21 (2H, m), 7.12 (1H, t, J=7.8 Hz), 7.05-7.08 (2H, m), 5.36 (1H, v br s), 4.88 (1H, v br s), 3.47 (3H, s). m/e (m+1): 409.2.

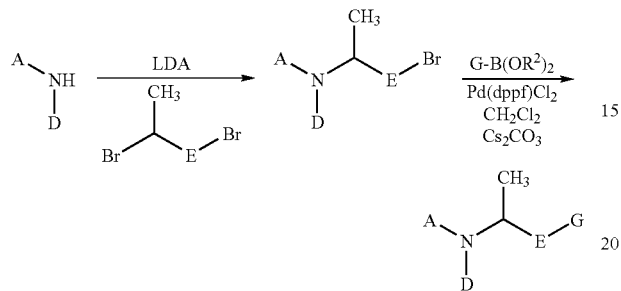

Variables A, D, E, and G are as defined above. R$^2$ represents C$_{1-6}$ alkylene, and together with B (boron) and O (oxygen) form a ring to which variable G is attached.

EXAMPLE 3

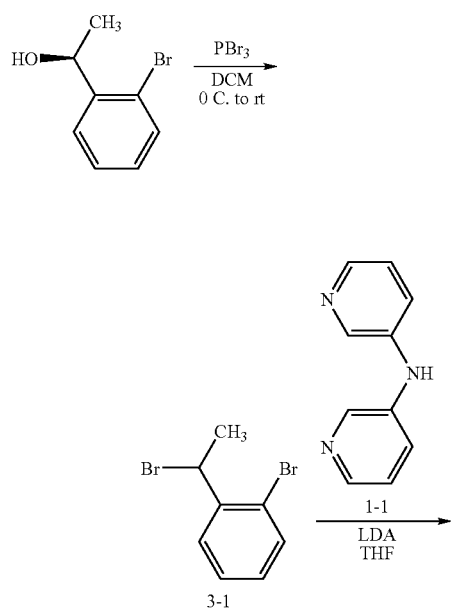

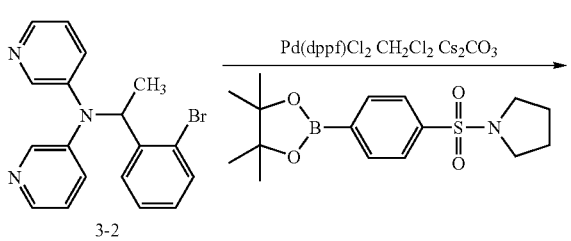

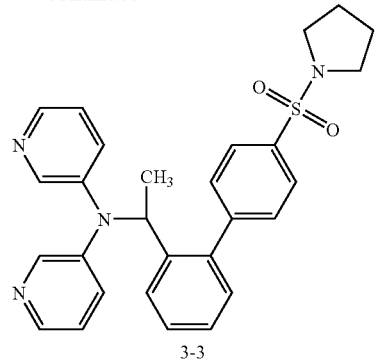

Preparation of 1-bromo-2-(1-bromoethyl)benzene (3-1)

To a cooled (0° C.) solution of(S)-1-(2-bromophenyl)ethanol (5.0 g, 24.86 mmol) in dry dichloromethane (20 mL), in N$_2$ atmosphere, was added phosphorus tribromide (4.67 mL, 49.7 mmol). The reaction was allowed to warm to room temperature and after 3 h, was diluted with water (20 mL) and NaHCO$_3$ sat. solution (10 mL). The mixture was extracted with dichloromethane (2×20 mL), washed with brine and the organic phase was dried over Na$_2$SO$_4$. Filtration, concentration and drying gave pure 1-bromo-2-(1-bromoethyl)benzene, as determined by $^1$H NMR, as a clear, yellow oil (6.42 g, 98%). 1H-NMR (300 Mz, CDCl$_3$): δ 7.66 (d, J=8.1 Hz, 1 H), 7.54 (d, J=6.6 Hz, 1 H), 7.35 (t, J=7.8 Hz, 1 H), 7.14 (t, J=6.3 Hz, 1 H), 5.61 (q, J=6.6 Hz, 1 H), 2.04 (d, J=6.9 Hz, 3 H).

Preparation of N-(1-(2-bromophenyl)ethyl)-N-(pyridin-3-yl)pyridin-3-amine (3-2)

To a cooled solution (−78° C.) of N-pyridin-3-ylpyridin-3-amine (0.886 g, 5.23 mmol) in dry tetrahydrofuran (20 mL) was added LDA (3.8 mL of a 1.5 M solution, 5.75 mmol) to form a light yellow suspension. After stirring for 30 min, 1-bromo-2-(1-bromoethyl)benzene (3-1) (1.38 g, 5.23 mmol) was added in one portion. The reaction was stirred for 30 min at −78° C. then allowed to warmn to 0° C. and quenched with NH$_4$Cl sat. solution (6 mL). The mixture was diluted with water and extracted with THF (2×20 mL), washed with brine and the organic layer was dried over Na$_2$SO$_4$. The solution was then filtered, concentrated, and dried under vacuum to give crude N-(1-(2-bromophenyl)ethyl)-N-(pyridin-3-yl)pyridin-3-amine (3-2) as a light brown solid (4.40 g): Analytical LCMS: (214 nm), 2.043 min. m/e (m+1): 356.1

N-pyridin-3-yl-N-{1-[4'-(pyrrolidin-1-ylsulfonyl)biphenyl-2-yl]ethyl}pyridin-3-amine (3-3)

In 0.5-2 mL microwave vial with stirbar was placed crude product N-(1-(2-bromophenyl)ethyl)-N-(pyridin-3-yl)pyridin-3-amine (3-2) (0.030 g, 0.08 mmol), 1-[4-(4,4,5,5,-tetramethyl-1,3,2-dioxaborolan-2-yl)benzenesulfonyl]pyrrolidine (0.040 g, 0.12 mmol), Pd (dppf) Cl$_2$ dichloromethane adduct (0.013 g, 0.0 16 mmol), Cs$_2$CO$_3$ (1 M aq. solution, 0.5 mL, 0.5 mmol) and THF (0.5 mL). The vial was sealed and heated in microwave to 160° C. for 10 min. The organic phase was filtered through packed celite, concentrated and dried. Reverse phase chromatography yielded a TFA salt Analytical LCMS: single peak (214 nm), 2.426 min. $^1$H NMR (300 MH, CDCl$_3$): δ 9.00 (s, 1 H), 8.65 (s, 1 H), 8.35 (d, J=5.1 Hz, 1 H), 8.17-8.25 (m, 2 H), 7.75-7.82 (m, 4 H), 7.56-7.7.67 (m, 4 H), 7.45-7.47 (m, 2 H), 7.28-7.31 (m, 1 H), 6.20 (q, J=6-6 Hz, 1 H), 3.19-3.24 (m, 4 H), 2.07 (d, J=6.6 Hz, 3 H), 1.76-1.80 (m, 4 H). m/e (m+1): 485.1.

Using the methodologies described below, representative compounds of the invention were evaluated and found to exhibit activity in the Kv1.5 assays, thereby demonstrating and confirming the utility of the compounds of this invention as Kv.15 inhibitors and antiarrhythmics. Compounds of this type may exhibit forward rate-dependence, blocking the outward K$^+$ currents to a greater extent or preferentially at faster rates of depolarization or heart rates. Such a compound could be identified in electrophysiological studies as described below. For example, during a train of depolarizations delivered at frequencies of 1 Hz and 3 Hz, the block is "rate-dependent" if the amount of block observed during a 10 second train at 3 Hz is greater than that at 1 Hz. A Kv1.5 blocker may also display use-dependence, during which the block of the outward K$^+$ currents increases with use, or during repetitive depolarization of a cardiac cell. Use dependence of block occurs to a greater extent with each successive depolarization in a train or sequence of pulses or depolarizations at a given rate or frequency. For example, during a train of 10 depolarizations at a frequency of 1 Hz, the block is "use-dependent" if the amount of block is greater for the 10$^{th}$ pulse than for the 1$^{st}$ pulse of the train. A Kv1.5 blocker may exhibit both use-dependence and rate-dependence.

A Kv1.5 blocker may also be identified through electrophysiological studies of native I$_{Kur}$, using cardiac myocytes or other tissue from various species including, but not limited to, human, rat, mouse, dog, monkey, ferret, rabbit, guinea pig, or goat. In native tissues Kv1.5 may exist as a homo-oligomer, or as a hetero-oligomer with other Kv family members, or may exist in a complex with a β-subunit. Compounds of this invention may block Kv1.5 homo- or hetero-oligomers or Kv1.5 in complexes with β-subunits.

Kv1.5 Assay

The high throughput Kv1.5 planar patch clamp assay is a systematic primary screen. It confirms activity and provides a functional measure of the potency of agents that specifically affect Kv1.5 potassium channels. Kiss et al. (Assay and Drug Dev. Tech., 1(1-2):127-135, 2003) and Schroeder et al. (J. of Biomol. Screen., 8(1);50-64, 2003) describe the use of this instrument for Kv1.5 as well as other voltage gated ion channels.

Chinese hamster ovary cells (CHO) stably expressing the human Kv1.5 potassium channel alpha subunit, cloned from human heart, are grown to 90-100% confluence in Ham's F12 medium supplemented with 10% FBS, 100 U/ml penicillin, 100 μg/ml streptomycin, 1000 μg/ml G-418 sulfate. Cells are subcultured by treatment with Versene, then suspended in phosphate-buffered saline (PBS) and centrifuged The cell pellet is resuspended in P13S and the resulting suspension placed in the cell reservoir of the IonWorks™ HT instrument.

Electrophysiological recordings are performed with intracellular solution containing (mM): K-gluconate 100, KCl 40, MgCl$_2$ 3.2, EGTA 3, N-2-hydroxyethylpiperazine-N$^1$-2-ethanesulphonic acid (HEPES) 5, adjusted to pH 7.3. Amphotericin (Sigma) is prepared as 30 mg/ml stock solution and diluted to a final working concentration of 0.1 mg/ml in internal buffer solution. The external solution is Dulbecco's PBS (Invitrogen) and contains (mM): CaCl$_2$ 0.90, KCl 2.67, K$_3$PO$_4$ 1.47, MgCl$_2$ 0.50, NaCl 138, Na$_3$PO$_4$ 8.10 and has a pH of 7.4. All compounds are prepared as 10 mM stock solutions in DMSO. Compounds are diluted into external buffer, then transferred from the drug plate to the Patchplate during the experiment (final DMSO concentration <0.66% vol.).

Kv1.5 ionic currents are recorded at room temperature. Membrane currents are amplified (RMS~10 pA) and sampled at 10 kHz. Leak subtraction was performed in all experiments by applying a 160 ms hyperpolarizing (10 mV) pre-pulses 200 ms before the test pulses to measure leak conductance. The patch clamp stimulus protocol is as follows:

1. Patchplate wells are loaded with 3.5 μL of external buffer.
2. Planar micropipette hole resistances (Rp) is determined by applying a 10 mV, 160 ms potential difference across each hole (Hole test).
3. Cells are pipetted into the Patchplate and form high resistance seals with the 1-2 μm holes at the bottom of each Patchplate well. A seal test scan is performed to determine how many of the Patchplate wells have cells that have formed seals.
4. In order to gain electrical access to the cells, intracellular solution containing amphotericin is circulated for 4 minutes on the bottom side of the Patchplate.
5. Pre-compound addition test pulse is applied to each well on the Patchplate. Protocol: Cells are voltage clamped at a membrane holding potential of −80 mV for 15 seconds. This is followed by application of a 5 Hz stimulus train (27×150 ms depolarizations to +40 mV). The membrane potential steps to +40 mV evoke outward (positive) ionic currents.
6. Compound is added to each well of the Patchplate Compounds are allowed to incubate for 5 minutes.
7. Post-compound addition test pulse protocol is applied. Protocol: Cells are voltage clamped at a membrane holding potential of −80 mV for 15 seconds. This is followed by application of a 5 Hz stimulus train (27×150 ms depolarizations to +40 mV).

Data analysis is conducted off-line. Paired comparisons between pre-drug and post-drug additions are used to determine the inhibitory effect of each compound. % inhibition of the peak control current during the 27$^{th}$ depolarization to +40 mV (in the 5 Hz train) is plotted as a function of antagonist concentration. The concentrations of drug required to inhibit current by 50% (IC$_{50}$) are determined by fitting of the Hill equation to the concentration response data: % of Control=100×(1+([Drug]/IC$_{50}$)$^P$)$^{-1}$ For each cell four arithmetic metrics are obtained:
1) seal resistance
2) baseline metric (the mean current at −70 mV from 5 to 45 ms before the first depolarization to +40 mV)
3) current run up metric (pre-compound mean current amplitude during the 1$^{st}$ depolarization to +40 mV minus the pre-compound mean current amplitude during the 27$^{th}$ depolarization to +40 mV)
4) peak current (maximum current amplitude during the 27$^{th}$ depolarization to +40 mV during the 5 Hz train).

All metrics are obtained during both the pre- and post-compound addition traces. Cells are eliminated from further analysis if:
1) seal resistance is <50 MΩ
2) baseline metric is >±100 pA during the pre-compound
3) current run up metric is >−0.2 nA
4) pre-read peak metric is <400 pA.

The above-listed compounds provide ≧20% inhibition at a concentration of 33 μM or less in the high throughput Kv1.5 planar patch clamp assay described above.

The compounds of this invention can be administered for the treatment or prevention of afflictions, diseases and illnesses according to the invention by any means that effects contact of the active ingredient compound with the site of action in the body of a warm-blooded animal. For example, administration, can be oral, topical, including transdermal, ocular, buccal, intranasal, inhalation, intravaginal, rectal, intracisternal and parenteral. The term "parenteral" as used herein refers to modes of administration which include subcutaneous, intravenous, intramuscular, intraarticular injection or infusion, intrasternal and intraperitoneal.

The compounds can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

For the purpose of this disclosure, a warm-blooded animal is a member of the animal kingdom possessed of a homeostatic mechanism and includes mammals and birds.

The dosage administered will be dependent on the age, health and weight of the recipient, the extent of disease, kind of concurrent treatment, if any, frequency of treatment and the nature of the effect desired. Usually, a daily dosage of active ingredient compound will be from about 1-500 milligrams per day. Ordinarily, from 10 to 100 milligrams per day in one or more applications is effective to obtain desired results. These dosages are the effective amounts for the treatment and prevention of afflictions, diseases and illnesses described above, e.g., cardiac arrhythmias such as atrial fibrillation, atrial flutter, atrial arrhythmia, supraventricular tachycardia, thromboembolic events such as stroke and congestive heart failure, auto-immune disorders such as immunoregulatory abnormalities, and cardiac insufficiency, in particular as a consequence of diastolic impairment.

Immunoregulatory abnormalities exist in a wide variety of autoimmune and chronic inflammatory diseases, including systemic lupus erythematosis, chronic rheumatoid arthritis, type I and It diabetes mellitus, inflammatory bowel disease, biliary cirrhosis, uveitis, multiple sclerosis and other disorders such as Crohn's disease, ulcerative colitis, bullous pemphigoid, sarcoidosis, psoriasis, ichthyosis, Graves ophthalmopathy and asthma. Compounds of the invention are useful for treating and preventing auto-immune disorders such as these immunoregulatory abnormalities.

The invention also includes use of a compound of the invention in the manufacture of a medicament, for treating a condition in a mammal, the treatment of which is effected or facilitated by $K_v1.5$ inhibition, such as cardiac arrhythmia or a thromboembolic event. The invention also includes use of a compound of the invention in the manufacture of a medicament, for preventing a condition in a mammal, the treatment of which is effected or facilitated by $K_v1.5$ inhibition, such as cardiac arrhythmia or a thromboembolic event.

The active ingredient can be administered orally in solid dosage forms, such as capsules, tablets, troches, dragées, granules and powders, or in liquid dosage forms, such as elixirs, syrups, emulsions, dispersions, and suspensions. The active ingredient can also be administered parenterally, in sterile liquid dosage forms, such as dispersions, suspensions or solutions. Other dosages forms that can also be used to administer the active ingredient as an ointment, cream, drops, transdermal patch or powder for topical administration, as an ophthalmic solution or suspension formation, i.e., eye drops, for ocular administration, as an aerosol spray or powder composition for inhalation or intranasal administration, or as a cream, ointment, spray or suppository for rectal or vaginal administration.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene gycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Suitable pharmaceutical carriers are described in *Remington's Pharmaceutical Sciences*, A. Osol, a standard reference text in this field.

For administration by inhalation, the compounds of the present invention may be conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of a compound of Formula I in suitable propellants, such as fluorocarbons or hydrocarbons.

For ocular administration, an ophthalmic preparation may be formulated with an appropriate weight percent solution or suspension of the compounds of Formula I in an appropriate ophthalmic vehicle, such that the compound is maintained in contact with the ocular surface for a sufficient time period to allow the compound to penetrate the corneal and internal regions of the eye.

Useful pharmaceutical dosage-forms for administration of the compounds of this invention include, but are not limited to, hard and soft gelatin capsules, tablets, parenteral injectables, and oral suspensions.

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

A mixture of active ingredient in a digestible oil such as soybean oil, cottonseed oil or olive oil is prepared and injected by means of a positive displacement pump into gelatin to form soft gelatin capsules containing 100 milligrams of the active ingredient. The capsules are washed and dried.

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

A parenteral composition suitable for administration by injection is prepared by stirring 1.5% by weight of active ingredient in 10% by volume propylene glycol. The solution is made to volume with water for injection and sterilized.

An aqueous suspension is prepared for oral administration so that each 5 milliliters contain 100 milligrams of finely divided active ingredient, 100 milligrams of sodium carboxymethyl cellulose, 5 milligrams of sodium benzoate, 1.0 grams of sorbitol solution, U.S.P., and 0.025 milliliters of vanillin.

The same dosage forms can generally be used when the compounds of this invention are administered stepwise or in conjunction with another therapeutic agent. When drugs are administered in physical combination, the dosage form and administration route should be selected depending on the compatibility of the combined drugs. Thus the term coadministration is understood to include the administration of the two agents concomitantly or sequentially, or alternatively as a fixed dose combination of the two active components.

Compounds of the invention can be administered as the sole active ingredient or in combination with a second active ingredient, including other antiarrhythmic agents having Kv1.5 blocking activities such as quinidine, propafenone, ambasilide, amiodarone, flecainide, sotalol, bretylium, dofetilide, almokalant, bepridil, clofilium, other compounds having Kv1.5 blocking activities such as clotrimazole, ketoconazole, bupivacaine, erythromycin, verapamil, nifedipine, zatebradine, bisindolylmaleimide, or other cardiovascular agents such as, but not limited to, ACE inhibitors such as benazepril, captopril, enalapril, fosinopril, lisinopril, moexipril, perindopril erbumine, quinapril, ramipril, and trandolapril, angiotensin II antagonists such as candesartan, eprosartan, irbesartan, losartan, olmesartan, telmisartan, and valsartan, cardiac glycosides such as digoxin, L-type calcium channel blockers, T-type calcium channel blockers, selective and nonselective beta blockers, an immunosuppressant compound, endothelin antagonists, thrombin inhibitors, aspirin, nonselective NSAIDs other than aspirin such as naproxen, warfarin, factor Xa inhibitors, low molecular weight heparin, unfractionated heparin, clopidogrel, ticlopidine, IIb/IIIa receptor antagonists such as tirofiban, 5HT receptor antagonists, integrin receptor antagonists, thromboxane receptor antagonists, TAFI inhibitors and P2T receptor antagonists Compounds of the invention can also be administered as the sole active ingredient or in combination with a pacemaker or defibrillator device.

What is claimed is:

1. A compound of formula I,

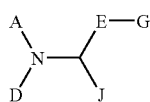

I or a pharmaceutically acceptable salt, wherein:
A is

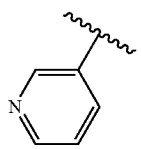

L is
1) an aryl ring,
2) a heteroaryl ring, wherein the point of attachment to the heteroaryl ring is a carbon atom, and the heteroaryl ring is selected from the group consisting of:
   a) a 5-membered unsaturated monocyclic ring with 1, 2, 3, or 4 heteroatom ring atoms selected from the group consisting of N, O or S,
   b) a 6-membered unsaturated monocyclic ring with 1, 2, 3, or 4 heteroatom ring atoms selected from the group consisting of N, O or S, and
   c) an 8-, 9- or 10-membered saturated or unsaturated bicyclic ring with 1, 2, 3, or 4 heteroatom ring atoms selected from the group consisting of N, O or S;
3) $C_1$-$C_{10}$ alkyl, wherein any stable atom is independently unsubstituted or substituted with a group selected from $R^4$,
4) a $C_3$-$C_{10}$ cycloalkyl ring, wherein any stable ring atom is independently unsubstituted or substituted with a group selected from $R^4$, and
5) a 4-6 membered saturated heterocyclic ring with 1,2 or 3 heteroatom ring atoms selected from the group consisting of N, O and S,
said aryl, heteroaryl, cycloalkyl, and saturated heterocyclic ring is unsubstituted, mono-substituted with $R^4$, disubstituted with groups independently selected from $R^4$, trisubstituted with groups independently selected from $R^4$, or tetrasubstituted with groups independently selected from $R^4$, and wherein any stable S or N heteroaryl or heterocyclic ring atom is unsubstituted or substituted with oxo;
D is

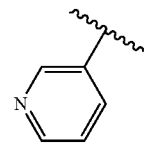

E is

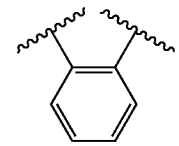

G, attached to a carbon atom of ring E, is selected from the group consisting of halogen,
—NH-L,
—N($SO_2C_{1-6}$alkyl)-L,
—N($C_{1-6}$alkyl)-L,
—NHC(O)NH-L,
—NH(C(O)$C_{1-6}$alkyl)-L,
—O-L,
—S-L,
—$SO_2$-L,
—C(O)NH-L,
—$C_{1-6}$alkylene-L, and
-L,
wherein $C_{1-6}$alkyl and $C_{1-6}$alkylene are unsubstituted or substituted with halogen;

J is selected from the group consisting of H, F, C$_{1-6}$ alkyl, CN, and CF$_3$;

R$^a$, in each instance in which it appears, is independently selected from the group consisting of
1) hydrogen,
2) C$_1$-C$_6$ alkyl,
3) halogen,
4) aryl,
5) heterocycle,
6) C$_3$-C$_{10}$ cycloalkyl,
7) OR$^5$, and
8) CH$_2$OR$^5$, said alkyl, aryl, heterocycle and cycloalkyl is unsubstituted or substituted with at least one substituent selected from R$^6$;

R$^4$, in each instance in which it appears, is independently selected from the group consisting of
1) hydrogen,
2) halogen,
3) NO$_2$,
4) CN,
5) CR$^4$=C(R$^5$)$_2$,
6) C≡CR$^5$,
7) (CR$^a_2$)$_n$OR$^5$,
8) (CR$^a_2$)$_n$N(R$^5$)$_2$,
9) (CR$^a_2$)$_n$C(O)R$^5$,
10) (CR$^a_2$)$_n$C(O)OR$^5$,
11) (CR$^a_2$)$_n$R$^5$,
12) (CR$^a_2$)$_n$S(O)$_m$R$^5$,
13) (CR$^a_2$)$_n$S(O)$_m$N(R$^5$)$_2$,
14) OS(O)$_m$R$^5$,
15) N(R$^5$)C(O)R$^5$,
16) N(R$^5$)S(O)$_m$R$^5$,
17) (CR$^a_2$)$_n$N(R$^6$)R$^5$,
18) (CR$^a_2$)$_n$N(R$^5$)(CR$^a_2$)$_n$C(O)N(R$^5$)$_2$,
19) (CR$^a_2$)$_n$N(R$^5$)(CR$^a_2$)$_n$C(O)OR$^5$,
20) N(R$^5$)(CR$^a_2$)$_n$R$^5$,
21) N(R$^5$)(CR$^a_2$)$_n$N(R$^5$)$_2$,
22) (CR$^a_2$)$_n$C(O)N(R$^5$)$_2$,
23) (CR$^a_2$)$_n$C(O)NH(CR$^a_2$)$_n$R$^5$,
24) (CR$^a_2$)$_n$C(O)NHC(R$^5$)$_2$(CR$^a$2)$_n$N(R$^5$)$_2$ and
25) C(O)NH(CR$^a_2$)(CR$^a_3$);

R$^5$, in each instance in which it appears, is independently selected from the group consisting of
1) hydrogen,
2) unsubstituted or substituted C$_1$-C$_6$ alkyl,
3) unsubstituted or substituted C$_3$-C$_{10}$ cycloalkyl,
4) unsubstituted or substituted aryl,
5) unsubstituted or substituted heterocycle,
6) CF$_3$,
7) unsubstituted or substituted C$_2$-C$_6$ alkenyl, and
8) unsubstituted or substituted C$_2$-C$_6$ alkynyl, or in the case where R$^5$ is attached to a nitrogen atom that is disubstituted with R$^5$, each R$^5$ is independently selected from C$_1$-C$_6$ alkyl, and the nitrogen atom together with each R$^5$ form a ring;

R$^6$, in each instance in which it appears, is independently selected from the group consisting of
1) hydrogen,
2) unsubstituted or substituted C$_1$-C$_6$ alkyl,
3) halogen,
4) oxo,
5) OR$^5$,
6) CF$_3$,
7) unsubstituted or substituted aryl,
8) unsubstituted or substituted C$_3$-C$_{10}$ cycloalkyl,
9) unsubstituted or substituted heterocycle, 10) S(O)$_m$N(R$^5$)$_2$,
11) C(O)OR$^5$,
12) C(O)R$^5$,
13) CN,
14) C(O)N(R$^5$)$_2$,
15) N(R$^5$)C(O)R$^5$,
16) N(R$^5$)C(O)OR$^5$,
17) N(R$^5$)C(O)N(R$^5$)$_2$,
18) OC(O)N(R$^5$)$_2$,
19) S(O)$_m$R$^5$,
20) OS(O)$_m$R$^5$,
21) NO$_2$,
22) N(R$^5$)$_2$;
23) SC(O)R$^5$,
24) N(R$^5$)S(O)$_m$R$^5$, m is independently 0, 1or 2; and n, in each instance in which it occurs, is independently selected from 0, 1, 2, 3, 4, 5 or 6.

2. A compound of claim 1, or a pharmaceutically acceptable salt thereof, wherein E-G is

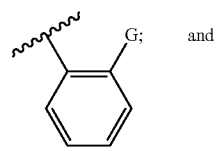

G is
halogen,
—NH-L,
—N(CH3)-L, or
-L.

3. A compound of claim 2, or a pharmaceutically acceptable salt thereof, wherein G is

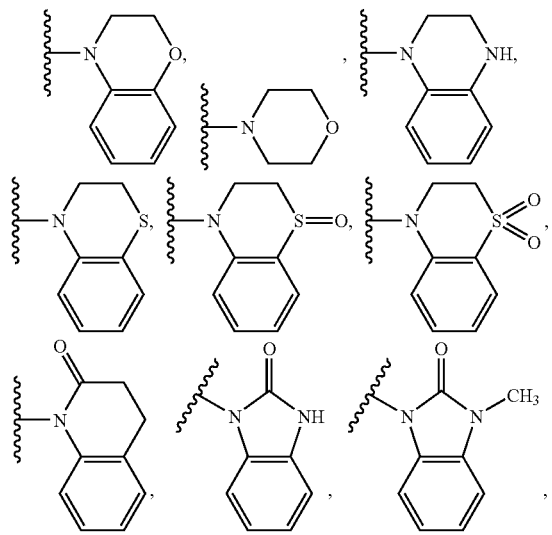

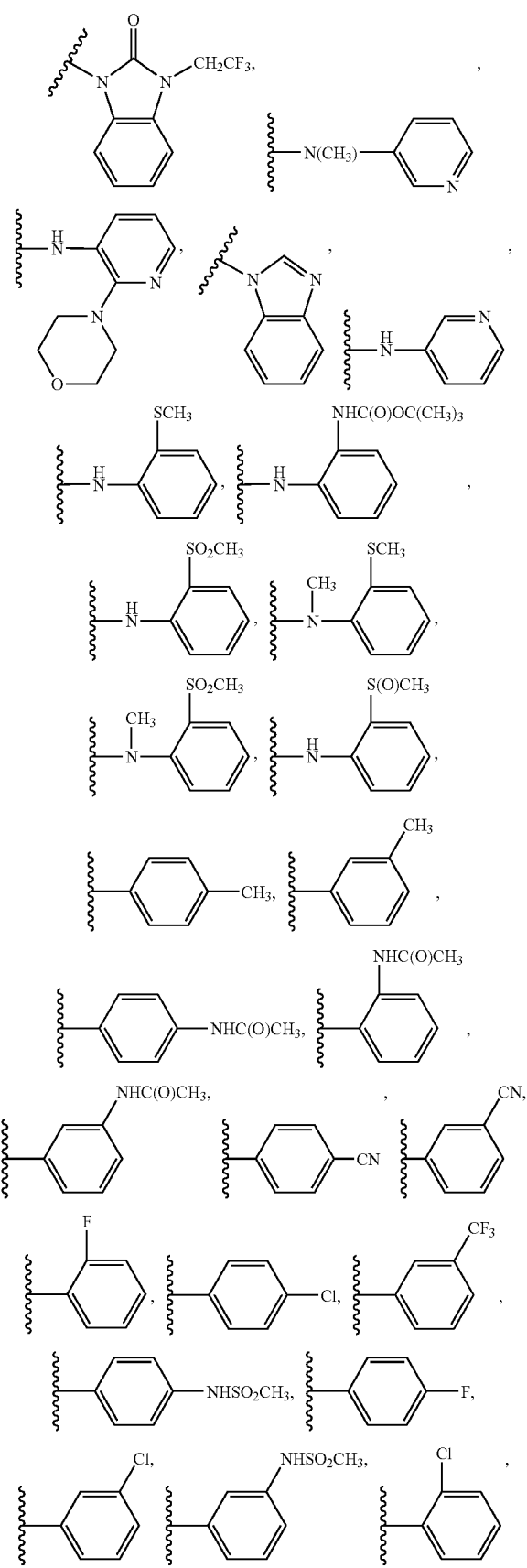
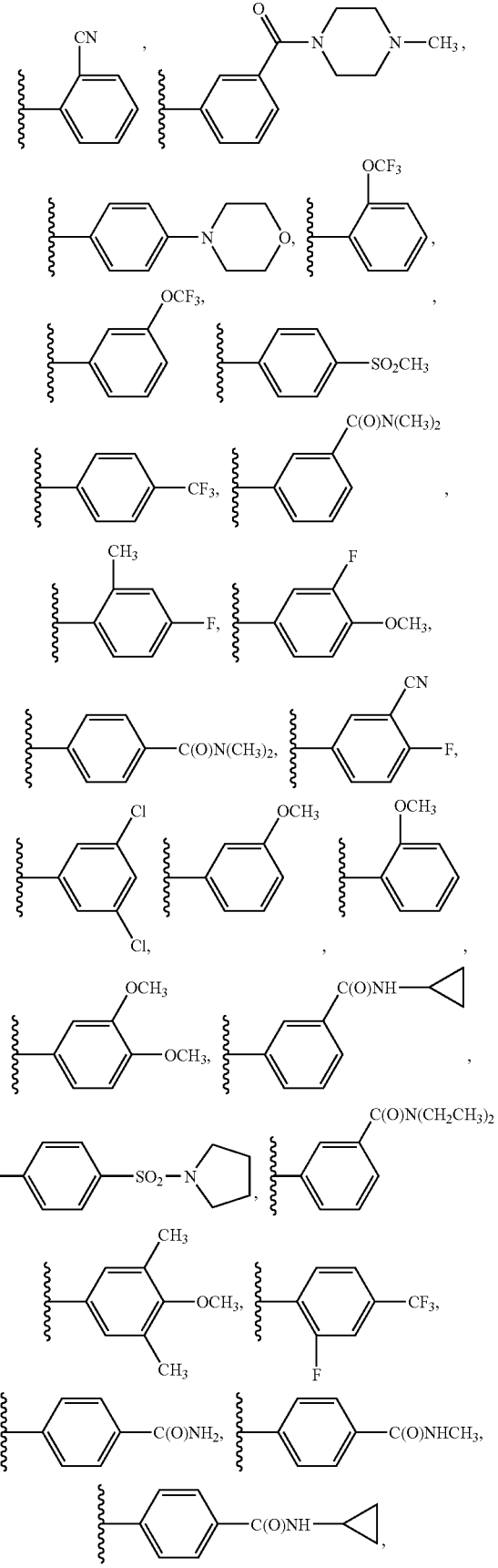

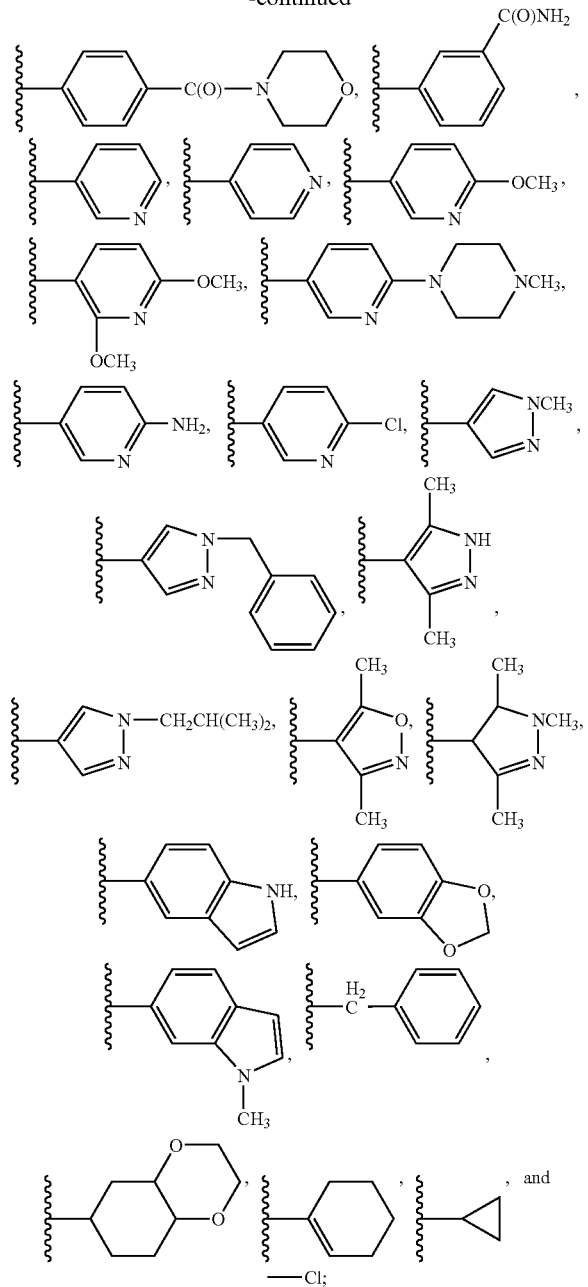

J is hydrogen or $C_{1-6}$ alkyl.

4. A compound of claim 1, or a pharmaceutically acceptable salt thereof, which is:
N-{2-[(dipyridin-3-ylamino)methyl]phenyl}-N-methylpyridin-3-amine,
N-[2-(2,3-dihydro-4H-1,4-benzothiazin-4-yl)benzyl]-N-pyridin-3-ylpyridin-3-amine,
N-[2-(1,1-dioxido-2,3-dihydro-4H-1,4-benzothiazin-4-yl)benzyl]-N-pyridin-3-ylpyridin-3-amine,
tert-butyl[2-({3-[(dipyridin-3-ylamino)methyl]pyridin-2-yl}amino)phenyl]carbamate,
N-(2-{[2-(methylsulfonyl)phenyl]amino}benzyl)-N-pyridin-3-ylpyridin-3-amine,
N-[1-(4-methylbiphenyl-2-yl)ethyl]-N-pyridin-3-ylpyridin-3-amine,
N-[1-(3-methylbiphenyl-2-yl)ethyl]-N-pyridin-3-ylpyridin-3-amine,
N-{2-[1-(dipyridin-3-ylamino)ethyl]biphenyl-4-yl}acetamide,
N-{1-[2-(1H-indol-5-yl)phenyl]ethyl}-N-pyridin-3-ylpyridin-3-amine,
N-{2-[1-(dipyridin-3-ylamino)ethyl]biphenyl-2-yl}acetamide,
N-pyridin-3-yl-N-[1-(2-pyridin-3-ylphenyl)ethyl]pyridin-3-amine,
N-{1-[2-(1-methyl-1H-pyrazol-4-yl)phenyl]ethyl}-N-pyridin-3-ylpyridin-3-amine,
N-{2-[1(dipyridin-3-ylamino)ethyl]biphenyl-3-yl}acetamide,
N-{1-[2-(1-benzyl-1H-pyrazol-4-yl)phenyl]ethyl}-N-pyridin-3-ylpyridin-3-amine,
N-pyridin-3-yl-N-[1-(2-pyridin-4-ylpheny)ethyl]pyridin-3-amine,
2-[1-(dipyridin-3-ylamino)ethyl]biphenyl-4-carbonitrile,
2-[1-(dipyridin-3-ylamino)ethyl]biphenyl-3-carbonitrile,
N-[1-(2-fluorobiphenyl-2-yl)ethyl]-N-pyridin-3-ylpyridin-3-amine,
N-[1-(4-chlorobiphenyl-2-yl)ethyl]-N-pyridin-3-ylpyridin-3-amine,
N-[1-(2-benzylphenyl)ethyl]-N-pyridin-3-ylpyridin-3-amine,
N-{1-[2-(6-methoxypyridin-3-yl)phenyl]ethyl}-N-pyridin-3-ylpyridin-3-amine,
N-pyridin-3-yl-N-{1-[3-(trifluoromethyl)biphenyl-2-yl]ethyl}pyridin-3-amine,
N-{2-[1-(dipyridin-3-ylamino)ethyl]biphenyl-4-yl}methanesulfonamide,
N-[1-(4-fluorobiphenyl-2-yl)ethyl]-N-pyridin-3-ylpyridin-3-amine,
N-[1-(3-chlorobiphenyl-2-yl)ethyl]-N-pyridin-3-ylpyridin-3-amine,
N-{2-[1-(dipyridin-3-ylamino)ethyl]biphenyl-3-yl}methanesulfonamide,
N-{1-[2-(3,5-dimethyl-1H-pyrazol-4-yl)phenyl]ethyl}-N-pyridin-3-ylpyridin-3-amine,
N-{1-[2-(1,3-benzodioxol-5-yl)phenyl]ethyl}-N-pyridin-3-ylpyridin-3-amine,
N-{1-[2-(2,3-dihydro-1,4-benzodioxin-6-yl)phenyl]ethyl}-N-pyridin-3-ylpyridin-3-amine,
N-{1-[2-(1-methyl-1H-indol-5-yl)phenyl]ethyl}-N-pyridin-3-ylpyridin-3-amine,
N-[1-(2-cyclohex-1-en-1-ylphenyl)ethyl]-N-pyridin-3-ylpyridin-3-amine,
N-[1-(2-chlorobiphenyl-2-yl)ethyl]-N-pyridin-3-ylpyridin-3-amine,
2-[1-(dipyridin-3-ylamino)ethyl]biphenyl-2-carbonitrile,
N-(1-{3-[(4-methylpiperazin-1-yl)carbonyl]biphenyl-2-yl}ethyl)-N-pyridin-3-ylpyridin-3-amine,
N-[1-(2-cyclopropylphenyl)ethyl]-N-pyridin-3-ylpyridin-3-amine,
N-{1-[2-(2,6-dimethoxypyridin-3-yl)phenyl]ethyl}-N-pyridin-3-ylpyridin-3-amine,
N-[1-(4-morpholin-4-ylbiphenyl-2-yl)ethyl]-N-pyridin-3-ylpyridin-3-amine,
N-(1-{2-[6-(4-methylpiperazin-1-yl)pyridin-3-yl]phenyl}ethyl)-N-pyridin-3-ylpyridin-3-amine,
N-pyridin-3-yl-N-{1-[2-(trifluoromethoxy)biphenyl-2-yl]ethyl}pyridin-3-amine,
N-pyridin-3-yl-N-{1-[3-(trifluoromethoxy)biphenyl-2-yl]ethyl}pyridin-3-amine,
N-{1-[2-(1-isobutyl-1H-pyrazol-4-yl)phenyl]ethyl}-N-pyridin-3-ylpyridin-3-amine, N-{1-[4-(methylsulfonyl)biphenyl-2-yl]ethy}-N-pyridin-3-ylpyridin-3-amine,
N-pyridin-3-yl-N-{1-[4-(trifluoromethyl)biphenyl-2-yl]ethyl}pyridin-3-amine,
2-[1-(dipyridin-3-ylamino)ethyl]-N,N-dimethylbiphenyl-3-carboxamide,
N-[1-(4-fluoro-2-methylbiphenyl-2-yl)ethyl]-N-pyridin-3-ylpyridin-3-amine,
N-[1-(3-fluoro-4-methoxybiphenyl-2-yl)ethyl]-N-pyridin-3-ylpyridin-3-amine,
2'-[1-(dipyridin-3-ylamino)ethyl]-N,N-dimethylbiphenyl-4-carboxamide,
2'-[1-(dipyridin-3-ylamino)ethyl]-4-fluorobiphenyl-3-carbonitrile,
N-[1-(3,5-dichlorobiphenyl-2-yl)ethyl]-N-pyridin-3-ylpyridin-3-amine,
N-[1-(3-methoxybiphenyl-2-yl)ethyl]-N-pyridin-3-ylpyridin-3-amine,
N-[1-(2-methoxybiphenyl-2-yl)ethyl]-N-pyridin-3-ylpyridin-3-amine,
N-[1-(3,4-dimethoxybiphenyl-2-yl)ethyl]-N-pyridin-3-ylpyridin-3-amine,
N-{1-[2-(3,5-dimethylisoxazol-4-yl)phenyl]ethy}-N-pyridin-3-ylpyridin-3-amine,
N-cyclopropyl-2-[1-(dipyridin-3-ylamino)ethyl]biphenyl-3-carboxamide,
N-pyridin-3-yl-N-{1-[4-(pyrrolidin-1-ylsulfonyl)biphenyl-2-yl]ethyl}pyridin-3-amine,
2-[1-(dipyridin-3-ylamino)ethyl]-N,N-diethylbiphenyl-3-carboxamide,
N-{1-[2-(6-chloropyridin-3-yl)phenyl]ethyl}-N-pyridin-3-ylpyridin-3-amine,
N-[1-(4-methoxy-3,5-dimethylbiphenyl-2-yl)ethyl]-N-pyridin-3-ylpyridin-3-amine,
N-pyridin-3-yl-N-{1-[2-(1,3,5-trimethyl-1H-pyrazol-4-yl)phenyl]ethyl}pyridin-3-amine,
N-{1-[2'-fluoro-4-(trifluoromethyl)biphenyl-2-yl]ethyl}-N-pyridin-3-ylpyridin-3-amine,
2-[1-(dipyridin-3-ylamino)ethyl]biphenyl-4-carboxamide,
2-[1-(dipyridin-3-ylamino)ethyl]-N-methylbiphenyl-4-carboxamide,
N-cyclopropyl-2'-[1-(dipyridin-3-ylamino)ethyl]biphenyl-4-carboxamide,
N-{1-[4-(morpholin-4-ylcarbonyl)biphenyl-2-yl]ethyl}-N-pyridin-3-ylpyridin-3-amine,
2-[1-(dipyridin-3-ylamino)ethyl]biphenyl-3-carboxamide, or
5-{2-[1-(dipyridin-3-ylamino)ethyl]phenyl}pyridin-2-amine.

5. A pharmaceutical formulation comprising a pharmaceutically acceptable carrier and the compound claim 1.

\* \* \* \* \*